US010712354B2

(12) United States Patent
Osawa et al.

(10) Patent No.: US 10,712,354 B2
(45) Date of Patent: Jul. 14, 2020

(54) METHOD OF ANALYZING DILUTED BIOLOGICAL SAMPLE COMPONENT

(71) Applicant: Leisure, Inc., Tokyo (JP)

(72) Inventors: Susumu Osawa, Yotsukaido (JP); Shinya Sugimoto, Tokyo (JP); Isao Yonekubo, Tokyo (JP)

(73) Assignee: Leisure, Inc., Tokyo (JP)

( * ) Notice: Subject to any disclaimer, the term of this patent is extended or adjusted under 35 U.S.C. 154(b) by 0 days.

(21) Appl. No.: 15/328,977

(22) PCT Filed: Jul. 6, 2015

(86) PCT No.: PCT/JP2015/069378
§ 371 (c)(1),
(2) Date: Jan. 25, 2017

(87) PCT Pub. No.: WO2016/013388
PCT Pub. Date: Jan. 28, 2016

(65) Prior Publication Data
US 2017/0205433 A1 Jul. 20, 2017

(30) Foreign Application Priority Data

Jul. 25, 2014 (WO) .................. PCT/JP2014/069718

(51) Int. Cl.
*G01N 33/49* (2006.01)
*G01N 33/96* (2006.01)
*C12Q 1/40* (2006.01)

(52) U.S. Cl.
CPC ............... *G01N 33/96* (2013.01); *C12Q 1/40* (2013.01); *C12Y 302/01023* (2013.01); *G01N 33/49* (2013.01); *G01N 2333/938* (2013.01); *G01N 2496/80* (2013.01)

(58) Field of Classification Search
CPC ............... A61K 2300/00; C07K 14/76; G01N 2800/60; G01N 2800/52; G01N 33/50; G01N 33/96; G01N 33/48; G01N 33/491; G01N 1/38; G01N 33/49; G01N 2333/765; A61B 5/150755; Y02A 90/26
See application file for complete search history.

(56) References Cited

U.S. PATENT DOCUMENTS 8,663,990 B2 * 3/2014 Yamamoto ....... G01N 27/44704
204/451
2002/0153316 A1 10/2002 Nanba et al.
2015/0064792 A1 3/2015 Hayakawa et al.

FOREIGN PATENT DOCUMENTS

| CN | 102866148 A | 1/2013 |
|---|---|---|
| EP | 0054096 | 6/1982 |
| EP | 1156335 | 11/2001 |
| EP | 2927683 | 10/2015 |
| JP | 59-20150 | 2/1984 |
| JP | 03-140844 | 6/1991 |
| JP | 06-148193 | 5/1994 |
| JP | 10-104226 | 4/1998 |
| JP | 2000-189196 | 7/2000 |
| JP | 2003-161729 | 6/2003 |
| JP | 2006-322829 | 11/2006 |
| JP | 4624644 | 11/2010 |
| JP | 2011-112451 | 6/2011 |
| WO | 02/24325 | 3/2002 |
| WO | 2009/116546 | 9/2009 |
| WO | 2011/065212 | 6/2011 |
| WO | 2013/012028 | 1/2013 |
| WO | 2014/073119 | 5/2014 |
| WO | 2016/013388 | 1/2016 |

OTHER PUBLICATIONS

Beer. Beer's Law. https://teaching.shu.ac.uk. 2006;1-6.*
European Search Report based on co-pending European Application No. 17189656.6, dated Mar. 21, 2018, 13 Pages.
Momii, Misato, et al., "Development of Method for Measuring Internal Standard Substance in Measurement of Biological Components in Diluted Sample Obtained by Fingertip Blood Collection", Journal of Analytical Bio-Science, Feb. 10, 2012, vol. 35, No. 1, p. 84 (Partial Translation).
Sugimoto, Shinya, et al., "Development of the Fingertip Blood Dilution Method for Blood Cell Counting", The Japanese Journal of Clinical Pathology, Mar. 25, 2014, vol. 62, No. 3, pp. 235-240.
Sugimoto, Shinya, et al., "Measurement of Biochemical Items and Hematocrit Using a Method for Diluting Two Internal Standards", Journal of Analytical Bio-Science, Feb. 10, 2012, vol. 35, No. 1, p. 85 (Full Translation).
Tomoe, Miki, et al., "New Function of Glutamic Acid, Which Has Been Found So Far", Clinical Neutrition, 2010, vol. 117, No. 5, pp. 549-564 (Partial Translation).
International Search Report, Based on co-pending International Application No. PCT/JP2015/069378, dated Sep. 8, 2015—4 Pages.
Supplemental European Search Report dated Nov. 28, 2017 based on co-pending European Application No. 15824166.1—pp. 1-10.
Supplemental European Search Report dated Dec. 8, 2017 based on co-pending European Application No. 17189658.2—pp. 1-9.
Ochs, Duane L., et al., "Ca2+-stimulated, Mg2+-dependent ATPase activity in neutrophil plasma membrane vesicles, Coupling to Ca2+ transport", Jan. 10, 1984, The Journal of Biological Chemistry, vol. 259, No. 1, pp. 102-106.

(Continued)

*Primary Examiner* — Lynn Y Fan
(74) *Attorney, Agent, or Firm* — McCarter & English, LLP

(57) ABSTRACT

There is provided a method of analyzing a biological sample component that allows easy and accurate quantification and counting of any of a plasma component and a blood cell component in a trace and unknown amount of a whole blood sample collected from a finger, for example. The method of the present invention is a method of analyzing a biological sample component in a trace amount of blood, comprising analyzing a diluent buffer into which the blood has been mixed and an internal standard substance and/or an external standard substance contained in the diluent buffer, calculating a dilution ratio, and analyzing a biological component in a plasma or serum component in the blood.

5 Claims, 15 Drawing Sheets

(56) References Cited

OTHER PUBLICATIONS

Chinese Office Action dated Nov. 5, 2018, relating to co-pending Chinese Patent Application No. 201580051060.9—6 Pages.
Xibao Bio Preferred Service Provider in China Life Science! Trinder's reagent; <http://www.seebio.cn/Article/trinderssj_1.html.> and English Translation. 6 pages. Accessed May 20, 2020.

* cited by examiner (a) (b) (c)

(a)   (b)   (c)

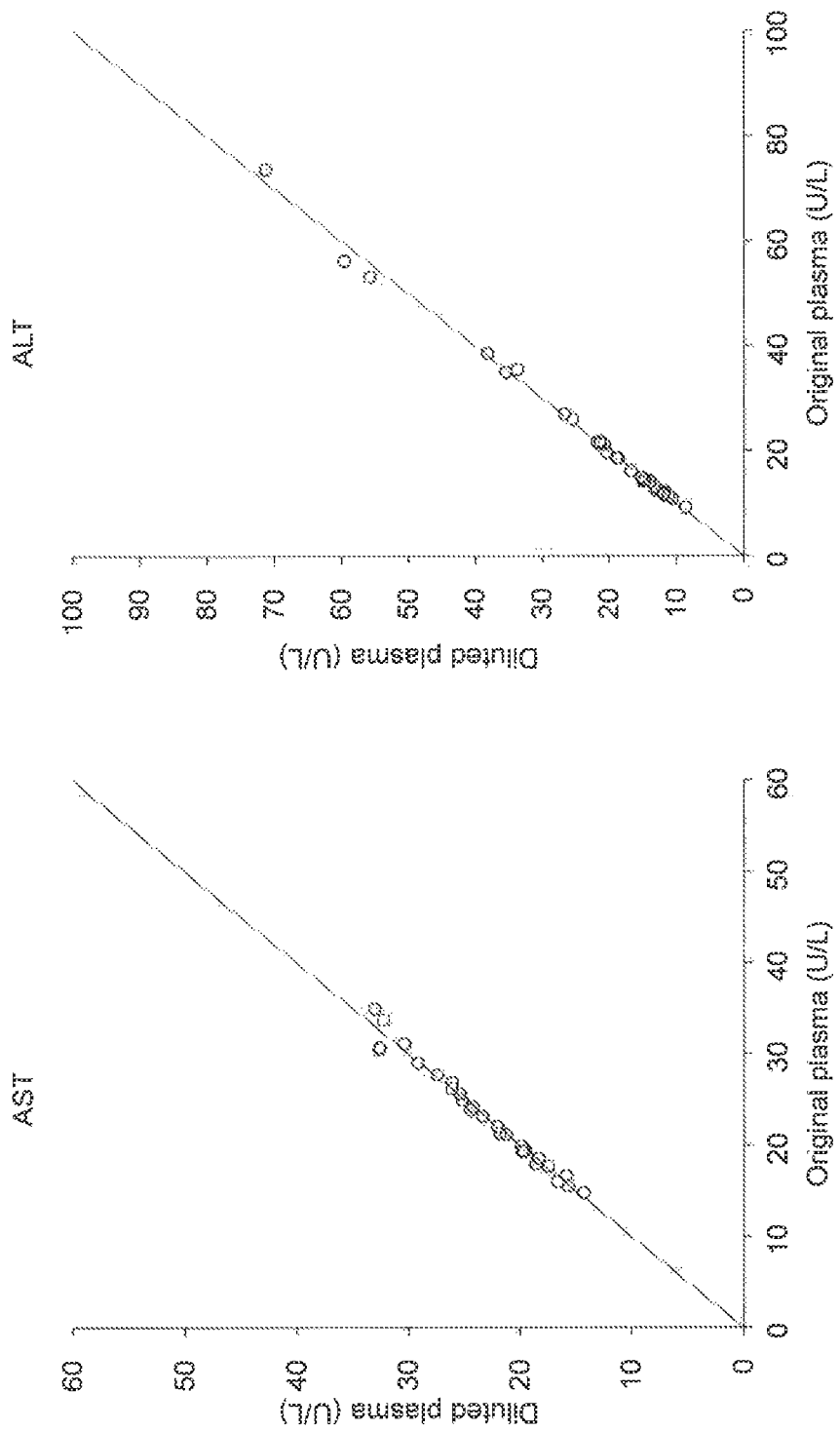

METHOD OF ANALYZING DILUTED BIOLOGICAL SAMPLE COMPONENT

RELATED APPLICATIONS

This application is a national stage application filed under 35 USC 371 of PCT/JP2015/069378, filed Jul. 6, 2015, which claims the benefit of PCT/JP2014/069718, filed Jul. 25, 2014, each of which are incorporated herein, in their entirety, by reference.

TECHNICAL FIELD

The present invention relates to a method of measuring a component to be analyzed in a biological sample such as blood, in which the biological sample is diluted with a buffer having a specific composition, and a plasma sample component or enzyme activity is analyzed from the mixed solution in the diluted sample.

The present invention also relates to a method of analyzing a trace amount of a biological sample component and to counting of blood cells, in which a biological sample such as an unquantified trace amount of blood is diluted with a predetermined buffer, and a plasma sample component is quantified and enzyme activity is analyzed from the mixed solution in the diluted sample.

BACKGROUND ART

For diagnosis of various diseases, determination of therapeutic effects, and health care, patients or subjects have to go to a medical institution or medical examination place to have their blood collected from the vein and tested. The patients or subjects, however, have to wait for a long time until they are informed of the test results. The patients or subjects also have to take a leave from work for the test, and require half a day or longer.

A method that allows testing of blood at any time at any place has been reported in which a trace amount of blood is diluted with a buffer containing an internal standard substance, and an unknown amount of a component present in the diluted plasma is quantified from the dilution factor of the internal standard substance (see Patent Literature 1, for example).

Specifically, as a method in which a trace amount of blood is diluted with a predetermined buffer, and a plasma sample component is quantified and enzyme activity is analyzed from the mixed solution in the diluted sample, a method that uses glycerol-3-phosphate or glycerol as an internal standard substance is known (see Patent Literature 2, for example).

For counting of the number of a blood cell component, a method that uses tyramine as the internal standard substance to be diluted is known (see Patent Literature 3, for example).

On the other hand, a method of testing from a trace amount of blood has been reported, which uses filter paper to collect blood (see Patent Literature 4, for example).

The use of a trace amount of blood allows a test to be performed regardless of the time and place, which is expected to contribute to the finding of a presymptomatic stage or the health maintenance.

CITATION LIST

Patent Literature

Patent Literature 1: JP Patent Publication (Kokai) No. 2003-161729 A
Patent Literature 2: JP Patent Publication (Kokai) No. 2006-322829 A
Patent Literature 3: JP Patent Publication (Kokai) No. 2011-112451 A
Patent Literature 4: JP Patent Publication (Kokai) No. 10-104226 A (1998)

SUMMARY OF INVENTION

Technical Problem

In the above-described conventional method of calculating a dilution ratio, however, glycerol-3-phosphate is used as the internal standard substance in the diluted solution of plasma, and glycerol-3-phosphate is hydrolyzed by alkaline phosphatase, which is an enzyme present in vivo, to produce glycerol. Thus, if the diluted solution is stored for a long time after the addition of blood, or if the temperature becomes high, an accurate dilution ratio of blood cannot be obtained. This reduces the reliability of the measured value of the biological component or enzyme activity in the original plasma. In order to overcome this situation, conventional methods require the addition of EDTA as an enzyme inhibitor. The addition of this inhibitor, however, does not allow complete enzyme inhibition. It is thus necessary to further add phosphoric acid as a product formation inhibitor. The addition of these two substances leads to a decrease in the activity of aspartate aminotransferase or alanine aminotransferase. As a result, it is necessary to add excess pyridoxal phosphate, which is an activator of these enzymes.

As an internal standard substance that solves these problems, a positively charged substance such as choline can be used. Such an internal standard substance, however, is not suitable for long-term storage in that it is adsorbed to a plastic container. These substances, which are claimed in [Patent Literature 2], are highly hydrophobic due to the presence of an aromatic ring in the molecule, and are adsorbed to a plastic container after long-term storage, which prevents an accurate determination of the dilution factor of blood. A compound such as ethanolamine has been found to be effective as a substance that does not have an aromatic ring in the molecule, and penetrates through blood cells. Such a substance is rarely present in blood, and is a stable compound. Such a substance is also soluble in a buffer for an internal standard solution, and is not adsorbed to a plastic container after long-term storage.

The present invention has been made to solve the above-described problems. An object of the present invention is to provide a method of calculating a dilution ratio that allows easy and accurate quantification of a component in a small and unknown amount of a diluted whole blood sample collected from a body surface of a subject such as a finger.

Moreover, in the method described in Patent Literature 3, although the stable compound, glycerol-3-phosphate, is used as an internal standard substance, if the amount of the sample is small, the dilution ratio of the internal standard substance will become small, which reduces the reliability of the dilution factor.

Furthermore, as described in Patent Literature 4, in the method in which blood is absorbed into filter paper or a porous material and is subsequently dried and sent by mail, and then a blood component is extracted, the component may be denatured during the drying process or during sending by mail. Additionally, it is necessary to use, as the buffer for extracting a biological component from the dried sample, a buffer containing NaOH, NaCl, or HCl, for adjusting the pH or stabilizing the biological component. For this reason, sodium or chloride concentration, which is the most hemostatic of all the components in the sample and does not significantly vary between individuals, cannot be used as an external standard substance for correcting the concentrations of other diluted original biological components.

On the other hand, in the method of diluting with a buffer, a biological component in a biological sample is stored in a buffer under physiological conditions at pH 7.4, which leads to excellent stability during transportation. In this method, however, the dilution ratio of the internal standard substance in the sample diluted with the buffer containing the internal standard substance is small, and thus, a measurement error tends to occur if the amount of the sample added is small.

An object of the present invention is to provide a method in which a biological sample is diluted with a buffer to quantitatively analyze a component to be analyzed in the biological sample, the method comprising determining a concentration of the biological component in the sample containing the biological component diluted with the buffer, by accurately determining the dilution factor of the biological sample from the dilution ratio of a hemostatic component as an external standard in the sample, to quantitatively analyze the component to be analyzed in the biological sample.

Another object of the present invention is to provide a method in which a biological sample is diluted with a buffer to quantitatively analyze a component to be analyzed in the biological sample, the method comprising accurately determining the dilution factor of the biological sample to quantitatively analyze the component to be analyzed in the biological sample, by compensating for drawbacks of both the method of determining the dilution factor of the biological sample using an internal standard substance and the method of determining the dilution factor of the biological sample using an external standard substance.

Solution to Problem

In order to achieve the above-described object, according to the present invention, analysis of a biological component in a biological sample such as blood is performed by: 1. using an internal standard substance; 2. using an external standard substance; or 3. using an internal standard substance and an external standard substance.

1. Method of Analysis using an Internal Standard Substance (Internal Standard Method)

The present invention provides a method of analyzing a biological component in a biological sample such as blood, which comprises analyzing a diluent buffer containing the biological sample such as blood and an internal standard substance contained in the diluent buffer, calculating a dilution ratio, calculating a dilution ratio of the biological component such as plasma, serum, or blood cells, and analyzing plasma or serum in the biological sample such as blood, or the biological component in the biological sample.

In the method of analyzing a biological sample component in a plasma sample according to the present invention, the internal standard substance in the butter is preferably a component that is stable for a long period of time, and that is not adsorbed to a container containing the buffer, is a substance that is rarely contained in the biological sample such as blood, and is a substance that can be analyzed easily and precisely using a biochemical automated analyzer, for example.

In the method of analyzing a biological sample component in a plasma sample according to the present invention, the internal standard substance in the buffer is preferably a component that does not penetrate through the blood cells, and is a substance that can accurately reflect the dilution ratio of the plasma or serum. Similarly, in the method of counting blood cells, the internal standard substance in the buffer is preferably a component that penetrates through the blood cells, and is a substance that can accurately reflect the dilution ratio of the whole blood (plasma and blood cells).

In the method of analyzing a biological sample component according to the present invention, the buffer preferably has an osmolality of 250 to 500 mOsm/kg relative to the blood cell membrane, and has a reagent composition that does not cause hemolysis of the blood cells upon mixing of blood.

In the method of analyzing a biological sample component according to the present invention, the buffer preferably has a composition that allows the biological sample component in the blood to be stably maintained without denaturation.

In the method of analyzing a biological sample component according to the present invention, the internal standard substance in the plasma preferably contains lithium or maltose.

From the dilution ratio of the plasma, the plasma concentration can be determined: however, the volume of blood cells cannot be determined. If the volume of the whole blood (plasma and blood cells) in the blood can be determined, it will be possible to test for anemia.

Thus, ethanolamine is preferably contained as the internal standard substance that penetrates into blood cells, which is hydrophobic and is not adsorbed to a plastic. The dilution ratio of the entire amount of blood can be determined by measuring this internal standard substance.

The volume ratio of blood cells (hematocrit value) can be determined from the dilution ratio of the plasma in the blood and the dilution ratio of the entire amount of blood.

In summary, the present invention is as set forth below.

[1-1] A method of analyzing a biological sample component, comprising:
using a diluent buffer into which a blood sample is to be mixed; analyzing an internal standard substance contained in the diluent buffer; calculating a dilution ratio of plasma or serum; and analyzing a biological component in a plasma or serum component in the blood sample, wherein
the internal standard substance contained in the diluent buffer has the property of not penetrating into blood cells, wherein the substance is selected from the group consisting of disaccharides including maltose, glutamic acid, leucine, valine, isoleucine, 4-hydroxybenzene, hydroxybutyric acid, creatine, malic acid, Trinder's reagents, and lithium.

[1-2] The method of analyzing a biological sample component according to [1-1], wherein
the internal standard substance contained in the diluent buffer is lithium.

[1-3] A method of analyzing a biological sample component comprising:
using a diluent buffer into which a blood sample is to be mixed, analyzing an internal standard substance contained in the diluent buffer; calculating a dilution ratio of blood; and analyzing a blood cell count or a biological component in plasma in the blood sample, wherein
the internal standard substance contained in the diluent buffer has the property of penetrating into blood cells, and is a substance selected from the group consisting of ethanolamine, hexylamine, phenylethylamine, amylamine, histamine, putrescine, hypoxanthine, tryptophan, pregnenolone, and β-sitosterol.

[1-4] A method of analyzing a biological sample component, comprising:

using a diluent buffer into which a blood sample is to be mixed; analyzing an internal standard substance contained in the diluent buffer; calculating a dilution ratio of blood, plasma, or serum, and analyzing a blood cell count or a biological component in plasma in the blood sample, or a biological component in a plasma or serum component in the blood sample, wherein the diluent buffer comprises:

the internal standard substance which has the property of not penetrating into blood cells, and is a substance selected from the group consisting of lithium, disaccharides including maltose, glutamic acid, leucine, valine, isoleucine, 4-hydroxybenzene, hydroxybutyric acid, creatine, malic acid, and Trinder's reagents; and the internal standard substance which has the property of penetrating into blood cells, and is a substance selected from the group consisting of ethanolamine, hexylamine, phenylethylamine, amylamine, histamine, putrescine, hypoxanthine, tryptophan, pregnenolone, and β-sitosterol.

[1-5] The method of analyzing a biological sample component according to [1-1], wherein the internal standard substance contained in the diluent buffer is an internal standard substance selected from compounds with a molecular weight of 500 or less and having a substituent in the molecule selected from the group consisting of a sulfate ion (—SO$^{3-}$), a carboxyl ion (—COO$^-$), a thiol group (—SH), and a quaternary amine (—NH$^{3+}$).

[1-6] The method of analyzing a biological sample component according to [1-1], wherein the internal standard substance contained in the diluent buffer is a Trinder's reagent, which is a compound selected from the group consisting of ADOS (N-ethyl-N-(2-hydroxy-3-sulfopropyl)-3-methoxyaniline), ADPS (N-ethyl-N-sulfopropyl-3-methoxyaniline), ALPS (N-ethyl-N-sulfopropylaniline), DAOS (N-ethyl-N-(2-hydroxy-3-sulfopropyl)-3,5-dimethoxyaniline), HDAOS (N-(2-hydroxy-3-sulfopropyl)-3,5-dimethoxyaniline), MAOS (N-ethyl-N-(2-hydroxy-3-sulfopropyl)-3,5-dimethylaniline), TOOS (N-ethyl-N-(2-hydroxy-3-sulfopropyl)-3-methoxyaniline), and TOPS (N-ethyl-N-sulfopropyl-3-methylaniline).

[1-7] The method of analyzing a biological sample component according to any of [1-1] to [1-6], wherein the diluent buffer has a reagent composition that does not cause hemolysis of the blood cells upon mixing of blood.

[1-8] The method of analyzing a biological sample component according to any of [1-1] to [1-7], wherein the diluent buffer comprises, depending on the component to be measured, an additive of a composition comprising a single or a combination of inhibitors selected from the group consisting of chelating agents such as ethylenediaminetetraacetate, citrate, and oxalate, antimicrobial agents or preservatives such as amikacin sulfate, kanamycin sulfate, thiabendazol, and sodium azide, coenzymes such as pyridoxal phosphate, magnesium, and zinc, saccharides such as mannitol, dextrose, and oligosaccharides, sodium dodecyl sulfate, mercury, and heparin, so that the biological sample component in the blood is not denatured and stably maintained.

[1-9] The method of analyzing a biological sample component according to [1-4], wherein a volume ratio of blood cells (hematocrit value) in the blood is calculated from the dilution ratio of the internal standard substance.

2. Method of Analysis using an External Standard Substance (External Standard Method)

It is known that sodium or chloride in blood has very high homeostasis, and does not significantly vary between individuals. Sodium also has a median concentration of 142 mmol/L, which is high for an in vivo concentration, and thus, allows precise measurement of a sample concentration with a high dilution factor even when diluted with a buffer. When sodium or chloride is used as an external standard, however, it has been impossible to use a buffer containing sodium or chloride as a diluent buffer.

The present inventors initially considered using sodium, chloride, or protein, which has high homeostasis in vivo, as an external standard substance.

In order to use these external standard substances, it has been necessary to avoid the presence of sodium or chloride in a buffer for diluting a biological sample. No buffer has previously existed which has a buffering capacity near pH 7.4 and free of alkalis (such as NaOH). The present inventors attempted to develop a new buffer, and used an amino alcohol compound such as 2-amino-2-methyl-1-propanol, 2-ethylaminoethanol, N-methyl-D-glucamine, diethanolamine, or triethanolamine, as an alkaline compound not containing an alkali metal (such as NaOH) or chloride ions. The inventors have made the new finding that when these compounds are mixed with a Good's buffer having excellent performance for biochemical research and having a pKa near pH 7.4, which is HEPES (2-[4-(2-hydroxyethyl)-1-piperazinyl]ethanesulfonic acid), TES (N-tris(hydroxymethyl)methyl-2-aminoethanesulfonic acid), MOPS (3-morpholinopropanesulfonic acid), or BES (N,N-bis(2-hydroxyethyl)-2-aminoethanesulfonic acid), as an acid, the resulting buffers can be adjusted to pH 7.4. The inventors have also found that these buffers are free of sodium or chloride, which is one example of an external standard substance, and do not interfere with a measurement system for sodium or chloride to be measured. Moreover, the inventors have found that components diluted with these buffers do not interfere with various measurement methods using biochemical and immunological automated analyzers, and that blood cells are not hemolyzed, and biological components can be stably stored at 37° C. Furthermore, for measuring biological components in plasma diluted with a buffer, the buffer components should not cause denaturation of these biological components, or affect the stability. As one example of this, the inventors have found that a buffer adjusted to pH 7.4 by mixing 2-amino-2-methyl-1-propanol (AMP) with HEPES is stable without causing denaturation of biological components, and does not also interfere with reagents for measuring these biological components.

The inventors have also found a method of accurately quantifying sodium at low concentration in a biological sample diluted with a diluent buffer.

In the present invention, sodium and the like in plasma, which maintain a certain concentration in the biological sample, are used as external standard substances. These substances are elements, and thus, are stable biological components. By determining the dilution factor of plasma by accurately measuring sodium or the like as an external standard substance diluted with a buffer, it is possible to quantify a biological sample component with an unknown concentration in the diluted plasma in the collected blood and analyze enzyme activity efficiently using a commercial biochemical or immunological automated analyzer, for a number of samples.

In summary, the present invention is as set forth below.

[2-1] A method of quantitative analysis of a component to be analyzed in a blood sample, in which a trace amount of the blood sample is diluted with a diluent buffer to quantitatively analyze the component to be analyzed in blood, the method comprising calculating a dilution factor of the blood sample using an external standard substance, wherein the external standard substance is a component homeostatically contained at a predetermined concentration in the blood sample, the diluent buffer is free of a component that interferes with quantification of the external standard substance, and a concentration of the external standard substance in the blood sample diluted with the diluent buffer is measured, and the dilution factor of the blood sample is calculated based on a measured value of the concentration.

[2-2] A method of quantitative analysis of a component to be analyzed in a blood sample, the method comprising:

measuring a concentration of an external standard substance in a blood sample diluted with a diluent buffer; and calculating a dilution factor of the blood sample based on a measured value of the concentration.

[2-3] The method of quantitative analysis according to [2-1] or [2-2], wherein the external standard substance is selected from the group consisting of sodium, chloride, albumin, and total protein.

[2-4] The method of quantitative analysis according to [2-3], wherein the external standard substance is selected from the group consisting of sodium, chloride, and total protein.

[2-5] The method of quantitative analysis according to any of [2-1] to [2-4], wherein the diluent buffer comprises, as buffering agent components, an amino alcohol compound selected from the group consisting of 2-amino-2-methyl-1-propanol, 2-ethylaminoethanol, N-methyl-D-glucamine, diethanolamine, and triethanolamine, and a buffering agent selected from the group consisting of HEPES (2-[4-(2-hydoxyethyl)-1-piperazinyl]ethanesulfonic acid), TES (N-tris(hydroxymethyl)methyl-2-aminoethanesulfonic acid), MOPS (3-morpholinopropanesulfonic acid), and BES (N,N-bis(2-hydroxyethyl)-2-aminoethanesulfonic acid), and the diluent buffer has buffering action at pH 7.4.

[2-6] The method of quantitative analysis according to any of [2-1] to [2-4], wherein the diluent buffer is substantially free of sodium and chloride.

[2-7] The method of quantitative analysis according to any of [2-1] to [2-6], wherein the dilution factor of a trace amount of the blood sample is calculated using formula (I) shown below, the component to be analyzed in diluted plasma is quantified, and the value of quantification is multiplied by the dilution factor determined using formula (I) to quantify the component to be analyzed in original plasma:

$$X = \frac{A}{B} \quad (1)$$

wherein

A: absorbance of a median of the concentration of the external standard substance in plasma of healthy individuals;

B: absorbance of the external standard substance in the diluted plasma; and

X: a plasma dilution factor, wherein the diluted plasma refers to plasma obtained by diluting the blood sample with the diluent buffer, and removing blood cells therefrom.

[2-8] The method of quantitative analysis according to any of [2-3] to [2-7], wherein sodium in the blood sample diluted with the diluent buffer is measured using a method shown below, by utilizing a phenomenon in which β-galactosidase undergoes a change in enzymatic activity in accordance with sodium ion concentration, and the sodium ion concentration can be quantified from variation in absorbance thereof:

a biological sample is diluted with the diluent buffer and is further diluted with purified water; a first reagent of a buffer comprising β-galactosidase is added in an amount 10 to 30 times the amount by volume of the sample; the mixture is heated at 30 to 45° C. for 2 to 20 minutes; a second reagent of a substrate solution comprising o-nitrophenyl-β-D-galactopyranoside is added in half the amount of the first reagent; and absorbance is measured at a primary wavelength of 410 nm and a secondary wavelength of 658 nm based on the reaction rate.

[2-9] A diluent buffer used for diluting a trace amount of the blood sample in the method of quantitative analysis according to any of [2-1] to [2-8], wherein the diluent buffer comprises, as buffering agent components, an amino alcohol compound selected from the group consisting of 2-amino-2-methyl-1-propanol, 2-ethylaminoethanol, N-methyl-D-glucamine, diethanolamine, and triethanolamine, and a buffering agent selected from the group consisting of HEPES (2-[4-(2-hydoxyethyl)-1-piperazinyl]ethanesulfonic acid), TES (N-tris(hydroxymethyl)methyl-2-aminoethanesulfonic acid), MOPS (3-morpholinopropanesulfonic acid), and BES (N,N-bis(2-hydroxyethyl)-2-aminoethanesulfonic acid), and the diluent buffer has buffering action at pH 7.4.

[2-10] The buffer according to [2-9], which is substantially free of sodium and chloride.

3. Method of Analysis using an Internal Standard Substance and an External Standard Substance (Hybrid Method)

As described above, the method of analysis using an internal standard substance alone and the method of analysis using an external standard substance alone have allowed accurate measurement of the component to be analyzed in a trace amount of the biological sample.

The present inventors aimed to achieve more accurate measurement, and conducted extensive research on a method having both the advantages of the method using an internal standard substance and the method using an external standard substance, by compensating for drawbacks of the method using an internal standard substance and the method using an external standard substance.

As described above, accurate measurement has been enabled by using sodium, chloride, or protein, which has high homeostasis in vivo, as an external standard substance, and using a buffer free of the substance used as the external standard substance. However, even though these substances have high homeostasis in healthy individuals, in some subjects, the range of concentrations of these substances may fall outside that of healthy individuals, which may result in a failure to provide accurate measurement.

On the other hand, the concentration of the internal standard substance in the diluent buffer can be set high, and thus, can be precisely measured. If the amount of the biological sample is small, however, the dilution of the internal standard substance will become small, which reduces the reliability of the dilution factor. As an internal standard substance of an organic compound, glycerol-3-phosphate can be used as a stable substance, and as an internal standard substance of an inorganic substance, lithium can be suitably used.

The present inventors conducted extensive research on the development of a method that can overcome the drawbacks of the method using an external standard substance alone and the method using an internal standard substance alone.

The present inventors considered using an element belonging to alkali metals or alkaline earth metals having high stability to overcome the drawbacks of the conventional internal standard substances, and using sodium, chloride, or protein having high homeostasis in vivo as an external standard substance.

The use of the internal standard substance in combination with the external standard substance, which is a component with high homeostasis in the biological sample, provides a method of quantification with high measurement precision, which allows a diluted component to be quantified with high reliability, by compensating for the drawbacks of the two quantification methods using an internal standard substance and an external standard substance. Thus, the present inventors completed the present invention.

The present invention has the following features. Sodium or the like in plasma, which maintains a certain concentration in a biological sample, is used as an external standard substance, and an element belonging to alkali metals or alkaline earth metals, such as lithium, or stable glycerol-3-phosphate is used as an internal standard substance that is not at all contained or rarely contained in plasma and does not pass through the blood cell membrane, and these substances are added into a buffer. The problem with storage stability has remained for the use of organic compounds conventionally used as internal standard substances, which are susceptible to enzymatic action. The internal standard substance described above is stable for a long period of time in the buffer, and can be easily quantified. Moreover, sodium used as the external standard substance in the biological sample to be measured is an element and thus, is also stable. As a result, it is possible to quantify a biological sample component with an unknown concentration in the diluted plasma in the collected blood and analyze enzyme activity efficiently using a commercial biochemical or immunological automated analyzer, for a number of samples.

In summary, the present invention is as set forth below.

[3-1] A method of quantitative analysis of a component to be analyzed in a blood sample, in which the sample is diluted with a diluent buffer to quantitatively analyze the component to be analyzed in blood, the method comprising calculating a dilution factor of the blood sample using an internal standard substance and an external standard substance, wherein a predetermined concentration of the internal standard substance is added into the diluent buffer, the external standard substance is a component homeostatically contained at a predetermined concentration in the blood sample, the diluent buffer is free of a component that interferes with quantification of the internal standard substance and the external standard substance, and a concentration of the internal standard substance and a concentration of the external standard substance in the blood sample diluted with the diluent buffer are measured, and the dilution factor of the blood sample is calculated based on measured values of these concentrations.

[3-2] A method of quantitative analysis, wherein the component to be analyzed in the blood sample is quantitatively analyzed by correcting the dilution factor of the blood sample determined based on the measured value of the concentration of the internal standard substance, using the measured value of the concentration of the external standard substance.

[3-3] The method of quantitative analysis according to [3-1] or [3-2], wherein the internal standard substance is selected from the group consisting of elements belonging to alkali metals or alkaline earth metals, and the external standard substance is selected from the group consisting of sodium, chloride, albumin, and total protein.

[3-4] The method of quantitative analysis according to [3-3], wherein the internal standard substance is lithium or glycerol-3-phosphate, and the external standard substance is sodium.

[3-5] The method of quantitative analysis according to any of [3-1] to [3-4], wherein the diluent buffer comprises, as buffering agent components, an amino alcohol compound selected from the group consisting of 2-amino-2-methyl-1-propanol, 2-ethylaminoethanol, N-methyl-D-glucamine, diethanolamine, and triethanolamine, and a buffering agent selected from the group consisting of HEPES (2-[4-(2-hydoxyethyl)-1-piperazinyl] ethanesulfonic acid), TES (N-tris(hydroxymethyl)methyl-2-aminoethanesulfonic acid), MOPS (3-morpholinopropanesulfonic acid), and BES (N,N-bis(2-hydroxyethyl)-2-aminoethanesulfonic acid), and the diluent buffer has buffering action between pH 6.5 and 8.0.

[3-6] The method of quantitative analysis according to [3-5], wherein the diluent buffer is substantially free of sodium and chloride.

[3-7] The method of quantitative analysis according to any of [3-1] to [3-6], wherein the dilution factor of a trace amount of the blood sample is calculated using any of formulae (1) to (4) shown below, the component to be analyzed in diluted plasma is quantified, and the value of quantification is multiplied by the dilution factor determined using any of the formulae (1) to (4) to quantify the component to be analyzed in original plasma:

Formula (1):

$$X = \frac{A+C}{B+D}; \qquad (1)$$

Formula (2):

$$X = \frac{\sqrt{(A^2+C^2)}}{\sqrt{(B^2+D^2)}}; \qquad (2)$$

Formula (3):

$$X = a \times (B+D) \pm b \qquad (3)$$

wherein a and b are coefficients; and data of B+D and the dilution factor are acquired in advance to prepare a standard curve represented by $X = a \times (B+D) \pm b$; and Formula (4):

$$X = A/B' \quad (4)$$

wherein $B' = (A \times D)/C$, wherein A, B, C, D, B', and X in the formulae shown above are defined as follows:

A: absorbance of the internal standard substance in the buffer containing the internal standard substance;

B: absorbance of the internal standard substance in the diluted plasma;

C: absorbance of a normal median of the concentration of the external standard substance in plasma;

D: absorbance of the external standard substance in the diluted plasma;

B': a correction value for correcting the absorbance of the internal standard substance in the diluted plasma, obtained by using the dilution factor calculated from the absorbance of the external standard substance; and X: a plasma dilution factor, wherein the diluted plasma refers to plasma obtained by diluting the blood sample with the diluent buffer, and removing blood cells therefrom.

[3-8] The method of quantitative analysis according to [3-1] to [3-7], wherein sodium, which is one of external standards in the blood sample diluted with the diluent buffer, is measured using a method shown below, by utilizing a phenomenon in which β-galactosidase undergoes a change in enzymatic activity in accordance with sodium ion concentration, and the sodium ion concentration can be quantified from variation in absorbance thereof:

a biological sample is diluted with the diluent buffer and is further diluted with purified water; a first reagent of a buffer comprising β-galactosidase is added in an amount 10 to 30 times the amount by volume of the sample; the mixture is heated at 30 to 45° C. for 2 to 20 minutes; a second reagent of a substrate solution comprising o-nitrophenyl-β-D-galactopyranoside is added in half the amount of the first reagent; and absorbance of the produced o-nitrophenol is measured at a primary wavelength of 410 nm and a secondary wavelength of 658 nm.

[3-9] A diluent buffer used for diluting a trace amount of the blood sample in the method of quantitative analysis according to [3-1] to [3-8], wherein the diluent buffer comprises, as buffering agent components, an amino alcohol compound selected from the group consisting of 2-amino-2-methyl-1-propanol, 2-ethylaminoethanol, N-methyl-D-glucamine, diethanolamine, and triethanolamine, and a buffering agent selected from the group consisting of HEPES (2-[4-(2-hydoxyethyl)-1-piperazinyl] ethanesulfonic acid), TES (N-tris(hydroxymethyl)methyl-2-aminoethanesulfonic acid), MOPS (3-morpholinopropanesulfonic acid), and BES (N,N-bis(2-hydroxyethyl)-2-aminoethanesulfonic acid), and the diluent buffer has buffering action at pit 7.4.

[3-10] The buffer according to [3-9], which is substantially free of sodium and chloride.

[3-11] The buffer according to [3-9] or [3-10], which is used for a method of quantitative analysis using an external standard substance.

[3-12] The buffer according to [3-9] or [3-10], which is used for a method of quantitative analysis using an internal standard substance.

Advantageous Effects of Invention

In the analysis of a biological sample component to be analyzed in a biological sample, the component is quantitatively analyzed by determining the dilution factor of the biological sample by using the internal standard substance or external standard substance, which allows the biological sample component to be accurately analyzed and measured, without measuring the biological sample analyte amount of a trace amount of the biological sample component.

Moreover, according to the present invention, easy and accurate quantification can be performed, using a plastic container, for plasma in the biological sample such as a trace and unknown amount of a whole blood sample collected from inside the body through a finger or the like, as well as any component in the biological sample. Furthermore, the volume ratio of blood cells (hematocrit value), which indicates the degree of anemia, can be determined through calculation from the dilution ratio of plasma and the dilution ratio of whole blood. Blood cell components (leukocyte count: WBC, erythrocyte count: RBC, amount of hemoglobin: Hgb, hematocrit: Hct) can also be counted by using the internal standard substance in whole blood.

Furthermore, the use of an internal standard substance alone or an external standard substance alone sometimes results in an insufficient precision or accuracy of quantification. In the present invention, both the internal standard substance and the external standard substance are used in combination to determine the dilution factor of the biological sample, such that the dilution factor determined with the internal standard substance is corrected based on the dilution factor determined with the external standard substance to provide a more accurate value, which allows quantification of the component to be analyzed with higher precision.

Furthermore, because no buffer has previously existed which has a buffering capacity at a near neutral pH of 7.4 and free of sodium or chloride, it has been impossible to use sodium or chloride, which is a substance having high homeostasis in vivo, as an external standard substance. In the method of the present invention, the use of the newly developed buffer having a buffering capacity at a near neutral pH of 7.4 and free of sodium or chloride has allowed the use of sodium or chloride having high homeostasis as an external standard substance, thus allowing analysis with higher precision and accuracy.

With the method of the present invention, many tests can be performed using a trace amount of blood (65 μL), such as for 13 items of biochemical tests, tumor markers, and hepatitis test. This testing method can be performed regardless of the time and place, and thus, can find a presymptomatic stage that cannot receive a medical examination. Furthermore, the ease of testing facilitates heath care, which allows a change within the body to be recognized before the disease becomes serious. This will also contribute to savings in national health care costs.

BRIEF DESCRIPTION OF THE DRAWINGS

FIG. 10-1 shows correlation diagrams between measured values of diluted plasma and measured values of original plasma determined using the hybrid method (total protein and albumin).

FIG. 10-2 shows correlation diagrams between measured values of diluted plasma and measured values of original plasma determined using the hybrid method (AST and ALT).

FIG. 10-3 shows correlation diagrams between measured values of diluted plasma and measured values of original plasma determined using the hybrid method (HDL-cholesterol and γ GTP).

FIG. 10-4 shows correlation diagrams between measured values of diluted plasma and measured values of original plasma determined using the hybrid method (total cholesterol and triglyceride).

FIG. 10-5 shows correlation diagrams between measured values of diluted plasma and measured values of original plasma determined using the hybrid method (urea nitrogen and creatinine).

FIG. 10-6 shows correlation diagrams between measured values of diluted plasma and measured values of original plasma determined using the hybrid method (uric acid and blood glucose).

DESCRIPTION OF EMBODIMENTS

Figure 1:
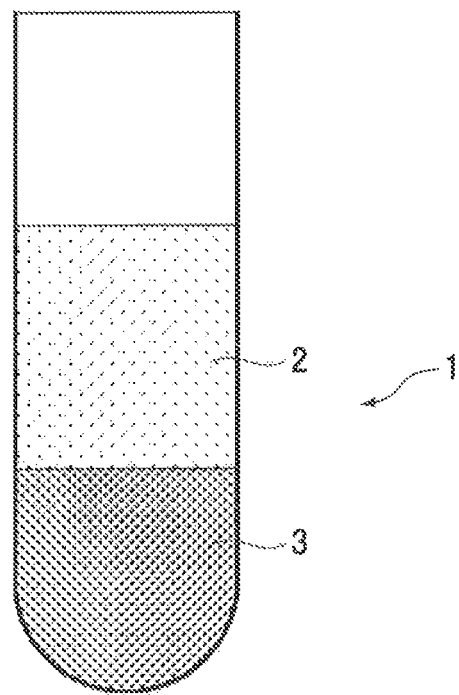
FIG. 1 is a schematic diagram showing the composition of blood used in the method of analyzing a biological sample component of the present invention.

1. Method of Analysis using an Internal Standard Substance (Internal Standard Method)

The present invention has the following features. Specifically, according to one feature of the present invention, there is provided a method of quantifying a component in an unknown concentration of a collected biological sample containing blood cells and analyzing enzyme activity, in which an internal standard substance is prepared which is a component not at all contained or rarely contained in the biological sample and does not pass through the blood cell membrane, and this internal standard substance is added into a buffer. The concentration of the internal standard substance in the buffer before the addition of blood is analyzed to obtain the absorbance, and the concentration of the internal standard substance in the diluted buffer after the addition of blood is measured to obtain the absorbance, and the plasma dilution ratio in the blood is determined from the ratio of these absorbances, to determine the quantity of the biological component or enzyme activity in original blood. In this case, the buffer is preferably prepared to have an osmolality substantially equal to the blood osmolality.

With the method of the present invention, it is unnecessary to determine the analyte amount of the biological sample to determine the dilution factor of plasma.

A method using the internal standard substance will be referred to as the "internal standard method". For example, a method using lithium as the internal standard substance will be referred to as the "lithium (Li) internal standard method".

The above-described sample with an unknown concentration may be a biological sample not containing blood cells (such as saliva or urine). The internal standard substance used in this case may be a substance that penetrates through the blood cell membrane.

A representative method of measuring the concentration of an internal standard substance in the buffer may be an enzymatic measurement method in which hydrogen peroxide is produced by adding an oxidase that uses as its substrate the internal standard substance or a substance derived from the internal standard substance, and the coloration of a quinone pigment, NAD(P)H, or a tetrazonium salt obtained by oxidative condensation of a Trinder's reagent and 4-aminoantipyrine in the presence of peroxidase is measured and quantified as the absorbance.

Other methods of quantifying the internal standard substance include a method in which the absorbance of the internal standard substance itself is directly measured; a method in which absorbance or chemiluminescence is measured by using an antibody and a labeled antibody for the internal standard substance; and chromatography. Any quantification method suitable for the internal standard substance used may be employed.

In order to accurately determine the dilution ratio of a plasma component in blood diluted with a buffer, the internal standard substance to be mixed into the buffer needs to be a substance that is either absent in vivo or present only in an extremely small amount in vivo, does not penetrate through the blood cell membrane, is stable in the buffer, and is not adsorbed to a container. The internal standard substance also needs to be a substance that does not interfere with other biological components.

As shown in FIG. 1, it is known that blood 1 is composed of plasma or serum 2, which is a liquid component, and blood cells 3, which are a solid component, and the blood cells 3 have a solid component such as the blood cell membrane and a liquid component inside the blood cell membrane. The addition of EDTA-2Na as an anticoagulant to blood 1 can inhibit coagulation of the blood cells 3. When this whole blood is centrifuged, the blood cells 3 having a greater specific gravity are sedimented in the bottom layer, and the plasma is separated in the supernatant.

Figure 2:
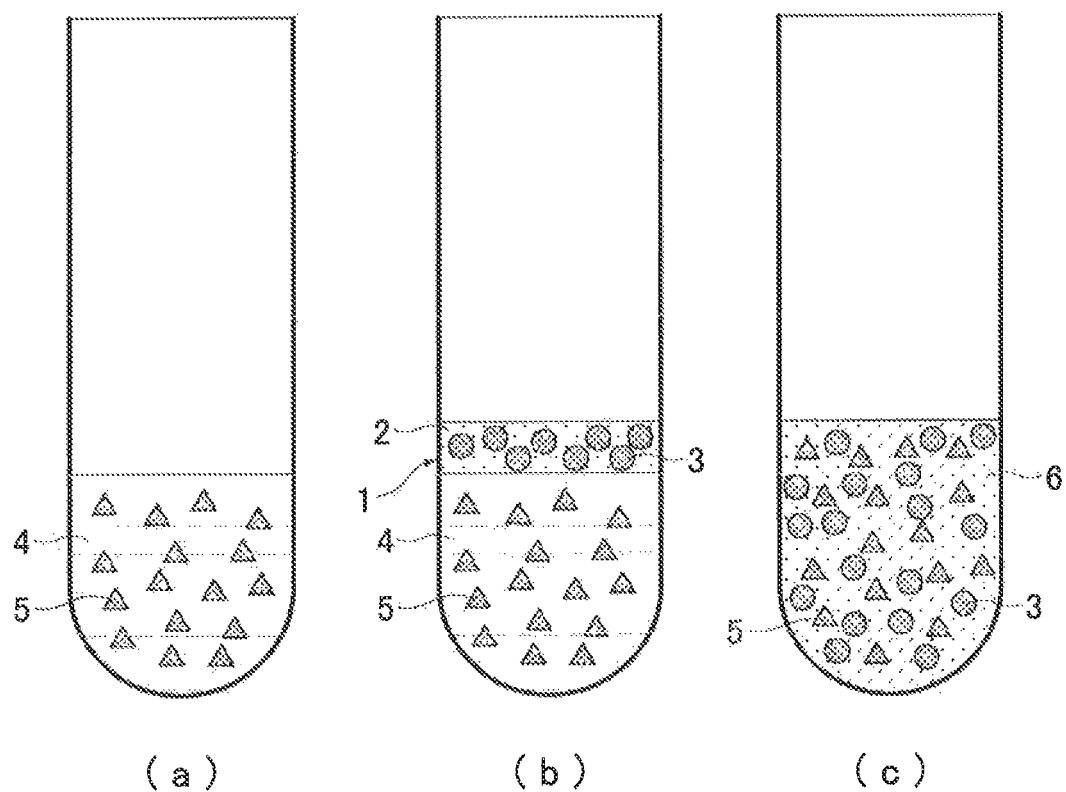
FIG. 2 is a schematic diagram showing the state in which the blood has been diluted with a predetermined buffer in the method of analyzing a biological sample component of the present invention, which diagram illustrates the case where an internal standard substance is used which does not penetrate through the blood cell membrane of the blood, and penetrates only into plasma.

As shown in FIG. 2, an internal standard substance 5 that does not penetrate through the blood cell membrane is placed in advance in a buffer 4 in a container (FIG. 2(a)), and the collected blood 1 is introduced from above the container into the upper side of the mixed layer of the buffer 4 and the internal standard substance 5 (FIG. 2(b)). When the blood 1 is then diluted with the predetermined buffer 4, the component that is originally present in the plasma or serum 2 and does not penetrate through the blood cell membrane is distributed throughout the buffer 4 and the plasma or serum 2, and is diluted, thus forming a diluted blood solution 6 (FIG. 2(c)).

In this case, when a prescribed amount of the internal standard substance 5 that does not penetrate through the blood cell membrane is dissolved in the buffer 4, the internal standard substance 5 originally present in the buffer is distributed throughout the buffer 4 and the plasma or serum 2, and is diluted. Maltose that penetrates only into the plasma 2, for example, is contained as the internal standard substance 5. Because maltose is dissolved as anions in the buffer 4, it is dissolved in the plasma 2, but does not penetrate into the blood cells 3.

The internal standard substance to be added into the buffer for the determination of the dilution ratio of the plasma component is a compound with a molecular weight of 500 or less and having a substituent in the molecule selected from the group consisting of a sulfate ion ($-SO^{3-}$), a carboxyl ion ($-COO^-$), a thiol group ($-SH$), and a quaternary amine ($-NH^{3+}$), which compound is selected from the group consisting of disaccharides such as maltose, glutamic acid, leucine, valine, isoleucine, 4-hydroxybenzene, hydroxybutyric acid, creatine, malic acid, metals (lithium, sodium, potassium, and chloride), and Trinder's reagents having a sulfate group in the molecule, such as (N-ethyl-N-(2-hydroxy-3-sulfopropyl)-3-methoxyaniline), ADPS (N-ethyl-N-sulfopropyl-3-methoxyaniline), ALPS (N-ethyl-N-sulfopropylaniline), DAOS (N-ethyl-N-(2-hydroxy-3-sulfopropyl)-3,5-dimethoxyaniline), HDAOS (N-(2-hydroxy-3-sulfopropyl)-3,5-dimethoxyaniline), MAOS (N-ethyl-N-(2-hydroxy-3-sulfopropyl)-3,5-dimethylaniline), TOOS (N-ethyl-N-(2-hydroxy-3-sulfopropyl)-3-methoxyaniline), and TOPS (N-ethyl-N-sulfopropyl-3-methylaniline). Among the above, lithium is preferred.

Figure 3:
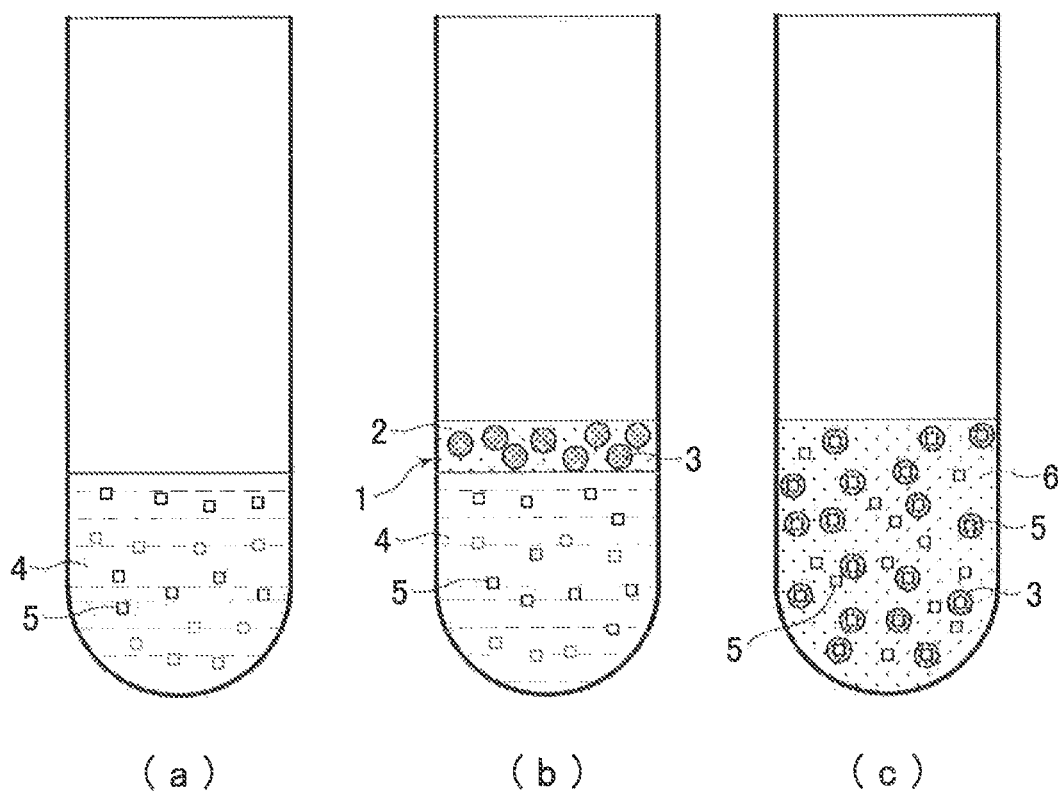
FIG. 3 is a schematic diagram showing the state in which the blood has been diluted with a predetermined buffer in the method of analyzing a biological sample component of the present invention, which diagram illustrates the case where an internal standard substance is used which has the property of penetrating into both plasma and blood cells of the blood.
Figure 4:
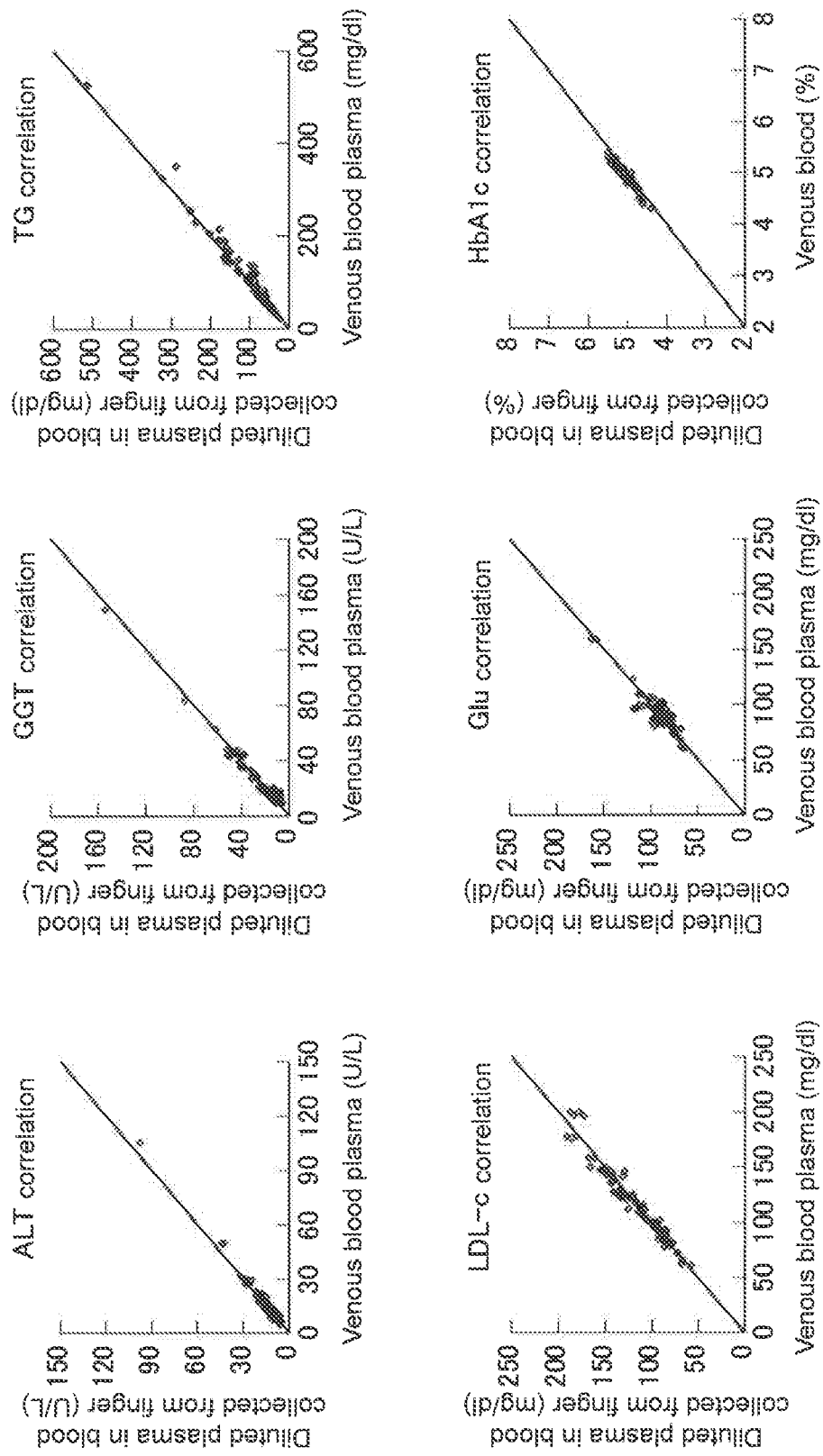
FIG. 4 shows correlation diagrams of biochemical tests between venous blood plasma and diluted plasma in the blood collected from a finger.

FIG. 3 is a diagram illustrating the distribution of the internal standard substance 5 throughout the whole blood (the plasma 2+the blood cells 3). The internal standard substance 5 (for example, ethanolamine) used in the case shown in FIG. 3 penetrates into both the plasma 2 and the blood cells 3. The internal standard substance 5 that penetrates through the blood cell membrane is placed in advance in the buffer 4 in a container (FIG. 3(a)), and the collected blood 1 is introduced from above the container into the upper side of the mixed layer of the buffer 4 and the internal standard substance 5 (FIG. 3(b)). When the blood 1 is then diluted with the predetermined buffer 4, the internal standard substance that is originally present in the plasma or serum 2 and penetrates through the blood cell membrane is present in both the blood cells 3 and the plasma or serum 2 and uniformly dispersed in the plasma or serum 2, thus forming a diluted blood solution 6 (FIG. 3(c)). Specifically, because the internal standard substance 5 used in the case shown in FIG. 3 is distributed in both the plasma 2 and the blood cells 3, the dilution factor diluted with the buffer 4 can be determined.

The internal standard substance that penetrates through the blood cell membrane may be a compound having a molecular weight of 500 or less and having a hydrophobic substituent such as an amino group ($-NH_2$), an alkyl group ($-CH_3$ or $-C_6H_6$), an ester group ($-COOR$), an alkoxy group ($-OR$), or halogen ($-Cl$, $-Br$, or $-I$), such as, for example, ethanolamine, hexylamine, phenylethylamine, amylamine, histamine, putrescine, hypoxanthine, tryptophan, pregnenolone, or β-sitosterol. Analysis can be performed with the enzymatic measurement method using an oxidase corresponding to any of these internal standards.

These internal standard substances are distributed in the blood cells and plasma, and therefore, can be used to determine the dilution factor of the whole blood (the plasma+the blood cells).

The buffer 4 for diluting a biological component needs to be miscible in any amount with the biological sample, and be able to stably keep the component to be measured in the biological sample. Examples of components of buffer 4 include, but are not limited to, those having a buffering capacity such as HEPES {2-[4-(2-hydoxyethyl)-1-piperazinyl]ethanesulfonic acid} buffer, ACES [N-(2-acetamido)-2-aminoethanesulfonic acid] buffer, ADA [N-(2-acetamido) iminodiacetic acid] buffer, BES [N,N-bis[2-hydroxyethyl]-2-aminosulfonic acid] buffer, Bicine [N,N-bis(2-hydroxyethyl)glycine] buffer, Bis-Tris [bis(2-hydroxyethyl) iminotris(hydroxymethyl)methane] buffer, CAPS (N-cyclohexyl-3-aminopropanesulfonic acid) buffer, CAPSO (N-cyclohexyl-2-hydroxy-3-aminopropanesulfonic acid) buffer, CHES (N-cyclohexyl-2-aminoethanesulfonic acid) buffer, DIPSO {3-[N,N-bis(2-hydroxyethyl)amino]-2-hydroxypropanesulfonic acid} buffer, EPPS {3-[4-(2-hydroxyethyl)-1-piperazinyl]propanesulfonic acid} buffer, HEPPSO {2-hydroxy-3-[4-(2-hydroxyethyl)-1-piperazinyl] propanesulfonic acid monohydrate} buffer, MES (2-morpholinoethanesulfonic acid monohydrate) buffer, MOPS (3-morpholinopropanesulfonic acid) buffer, MOPSO (2-hydroxy-3-morpholinopropanesulfonic acid) buffer, PIPES [piperazine-1,4-bis(2-ethanesulfonic acid)] buffer, POPSO [piperazine-1,4-bis(2-hydroxy-3-propanesulfonic acid) dihydrate] buffer, TAPS [N-tris(hydroxymethyl)methyl-3-aminopropanesulfonic acid] buffer, TAPSO [2-hydroxy-N-tris(hydroxymethyl)methyl-3-aminosulfonic acid] buffer, TES [N-tris(hydroxymethyl)methyl-2-aminoethanesulfonic acid] buffer, Tricine {N-[tris(hydroxymethyl)methyl]glycine} buffer, acetate buffer, phosphate buffer, citrate buffer, borate buffer, tartrate buffer, and phosphate buffered saline. Although the concentration of the buffer is not particularly limited, it is preferably 0.1 to 1000 mmol/L, and is particularly preferably 10 to 500 mmol/L. Although the pH of the buffer is not particularly limited, it is desirably near the original pH of the biological sample in view of stability of the biological sample to be diluted, and the pH is preferably 6 to 8 in the case of blood, plasma, or serum.

For the purpose of stably keeping the component to be measured, the diluent buffer may contain a chelating agent, an antimicrobial agent, a preservative, a coenzyme, a saccharide, an inhibitor, and the like.

Examples of chelating agents include ethylenediaminetetraacetate, citrate, and oxalate. Examples of antimicrobial agents or preservatives include amikacin sulfate, kanamycin sulfate, thiabendazol, and sodium azide. Examples of coenzymes include pyridoxal phosphate, magnesium, and zinc. Examples of saccharides include mannitol, dextrose, and oligosaccharides. Examples of inhibitors include sodium dodecyl sulfate, mercury, and heparin.

A combination of a plurality of types of stabilizers may be added depending on the component to be measured. When the blood, plasma, or serum is diluted with the buffer, and the components to be measured are AST (aspartate aminotransferase) and ALT (alanine aminotransferase), the buffer preferably contains ethylenediaminetetraacetate and pyridoxal phosphate. The buffer in this case desirably contains 0.1 to 5.0 mmol/L of ethylenediaminetetraacetate and 0.01 to 0.20 mmol/L of pyridoxal phosphate, and particularly preferably contains 0.5 to 3.0 mmol/L of ethylenediaminetetraacetate and 0.02 to 0.10 mmol/L of pyridoxal phosphate.

It is necessary for the internal standard substance to be added into the buffer to be absent in vivo or be present only in an extremely small amount in vivo, not to interfere with the biological component, to be stable in the buffer, not to be adsorbed to a storage container, and to permit the use of a detection system that allows accurate measurement. Moreover, for dilution of the blood, the internal standard substance needs to have an osmolality that does not dissolve blood cells, and preferably has an osmolality of 250 to 500 mOsm/kg.

Table 1 shows the composition of an example of the buffer containing sarcosine, which is one of internal standard substances that do not penetrate through the blood cell membrane, and ethanolamine, which is one of internal standard substances that penetrates through the blood cell membrane.

TABLE 1

Composition of a Buffer Containing Maltose and Ethanolamine

| Substance Name | Concentration |
|---|---|
| HEPES | 100 mM |
| Maltose | 3.87 mM |
| Ethanolamine | 4.37 mM |
| Sodium Chloride | 154 mM |
| EDTA-2Na | 1.34 mM |
| Pyridoxal Phosphate | 0.03 mM |
| Amikacin | 0.0012% |
| pH | 7.4 |

In Table 1, HEPES refers to N-2-hydroxyethylpiperazine-N'-2-ethanesulfonic acid.

Table 2 shows reagents for measuring sarcosine, which is one of internal standard substances that do not pass through the blood cell membrane.

TABLE 2

Reagents for Measuring Maltose

| R-1 | | R-2 | |
|---|---|---|---|
| Substance Name | Concentration | Substance Name | Concentration |
| MES-NaOH Buffer | 0.1 mol/L | MES-NaOH Buffer | 0.1 mol/L |
| Glucose Oxidase | 50 U/ml | Glucosidase | 15 U/mL |
| Glucose Oxidase | U/mL | 4-Aminoantipyrine | 4.0 mM |
| Mutarotase | 1.3 U/mL | Peroxidase | 16 U/mL |
| TOOS | 1.5 mM | pH | 6.5 |
| pH | 6.5 | | |

In Table 2, TOOS refers to N-ethyl-N-(2-hydroxy-3-sulfopropyl)-3-methylaniline sodium salt dihydrate.

The procedure for measuring maltose is given below.

R1 and R2 shown above are used for measuring maltose.

1. Mix 7.0 μl of the biological sample mixture with 90 μl of R1, and allow the mixture to stand at 37° C. for 5 minutes.
2. Measure the absorbance at 545/658 nm—A1 (absorbance).
3. Mix 30 μl of R2 and allow the mixture to stand at 37° C. for 5 minutes.
4. Measure the absorbance at 545/658 nm—A2 (absorbance).

The absorbance can be expressed as the difference between the measured values. Thus, the absorbance is generally obtained as ΔA=A2−A1.

Table 3 shows reagents for measuring ethanolamine, which is one of internal standard substances that pass through the blood cell membrane.

TABLE 3

Reagents for Measuring Ethanolamine

| R-1 | | R-2 | |
|---|---|---|---|
| Substance Name | Concentration | Substance Name | Concentration |
| HEPES•NaOH Buffer | 0.1 mol/L | HEPES•NaOH Buffer | 0.1 mol/L |
| DAOS | 1.6 mmol/L | 4-Aminoantipyrine | 0.4 mmol/L |
| Peroxidase | 5 U/mL | Tyramine Oxidase | 20 U/mL |
| Ascorbate Oxidase | 7.4 U/mL | | |
| pH | 7.9 | pH | 7.9 |

In Table 3, DAOS refers to N-ethyl-N-(2-hydroxy-3-sulfopropyl)-3,5-dimethylaniline salt.

The procedure for measuring ethanolamine is given below.

R1 and R2 shown above are used for measuring ethanolamine.

1. Mix 11 μl of the biological sample mixture with 90 μl of R1, and allow the mixture to stand at 37° C. for 5 minutes.
2. Measure the absorbance at 596/805 nm—A3 (absorbance).
3. Mix 45 μl of R2 and allow the mixture to stand at 37° C. for 5 minutes.
4. Measure the absorbance at 546/884 nm—A4 (absorbance).

The absorbance can be expressed as the difference between the measured values. Thus, the absorbance is generally obtained as ΔA=A4−A3.

It is known that the relationship between absorbance and concentration is $A = \varepsilon \times c \times l$ in accordance with the Lambert-Beer law, wherein A (absorbance), ε (molar extinction coefficient), c (molar concentration of the solute), and l (optical path length). The absorbance (A) and the molar concentration (c) of the solute are in proportional relationship, and in general, the concentration of the solute in an unknown sample can be calculated by using a calibration curve obtained by measuring solutions in which known concentrations of the solute are dissolved.

As shown in FIG. 1, it is known that blood 1 is composed of plasma 2 or serum, which is a liquid component, and blood cells 3, which are a solid component, and the blood cells 3 have a solid component such as the blood cell membrane and a liquid component inside the blood cell membrane. The addition of EDTA-2Na as an anticoagulant to the blood can inhibit coagulation of the blood cells. When this whole blood is centrifuged, the blood cells having a greater specific gravity are sedimented in the bottom layer, and the plasma is separated in the supernatant.

As shown in FIG. 2, when the blood 1 is diluted with the predetermined buffer 4, the component that is originally present in the plasma 2 or serum and does not penetrate through the blood cell membrane is distributed throughout the buffer 4 and the plasma 2 or serum, and is diluted.

In this case, when a prescribed amount of the internal standard substance 5 that does not penetrate through the blood cell membrane is dissolved in the buffer 4, the internal standard substance originally present in the buffer is distributed throughout the buffer and the plasma or serum, and is diluted. This internal standard represents an internal standard that penetrates only into the plasma, such as maltose. Because maltose is dissolved as anions in the buffer, it is dissolved in the plasma, but does not penetrate into the blood cells.

Specifically, an initial concentration (C0) of the internal standard substance 5 that does not penetrate through the blood cell membrane in the buffer 4 changes to a concentration (C1) upon the addition of the blood. A dilution ratio of the plasma or serum, (r1)=C0/(C0−C1), is calculated from C0 and C1. The amount of buffer is assumed as V0, and the total amount of the buffer to which the plasma or serum has been added is assumed as V1. Here, the dilution ratio of the component that is originally present in the plasma or serum and does not penetrate through the blood cell membrane is equal to the dilution ratio of the plasma 2 or serum, and hence, is calculated based on r1=(V0+V1)/V1=C0/(C0−C1).

When the blood 1 is diluted with the predetermined buffer 4, the component that penetrates through the blood cell membrane is distributed throughout the buffer and the plasma or serum and the blood cells, and is diluted. In this case, when a prescribed amount of the internal standard substance that penetrates through the blood cell membrane is dissolved in the buffer, the internal standard substance originally present in the buffer is distributed throughout the buffer and the plasma or serum and the blood cells, and is diluted. When the volume of the blood cell membrane is assumed as (V2) and the volume of the inside of the blood cells is assumed as (V3), an initial concentration (C2) of the internal standard substance that penetrates through the blood cell membrane in the buffer changes to a concentration (C3) upon the addition of the blood. A dilution ratio of the entire blood. (r2)=(V0+V1+V2+V3)/(V1+V2+V3)=C2/(C2−C3), is calculated from C2 and C3. Here, the dilution ratio of the component that is originally present in the plasma or serum and the blood cell liquid and penetrates through the blood cell membrane is equal to the dilution ratio of the entire blood, and hence, is calculated based on r2=(V0+V1+V2+V3)/(V1+V2+V3)=C2/(C2−C3).

These formulae are applicable to all of the cases shown in Table 4 below.

stance is a prescribed amount, the volume of the blood (V1+V2+V3) can be calculated from the dilution ratio (r2) of the blood calculated based on the internal standard substance that penetrates through the blood cell membrane.

Specifically, V1+V2+V3=V0/(r2−1) can be calculated.

When the biological sample is diluted with a solution containing the internal standard substance that does not penetrate through the blood cell membrane and the internal standard substance that penetrates through the blood cell membrane, V2+V3=(V1+V2+V3)−V1=V0/(r2−1)−V0/(r1−1) can be calculated from both the formulae, V1, determined from V0 and r1, and V1+V2+V3, determined from V0 and r2.

It is also known that blood cells are composed of 65% of the liquid and 35% of the solid.

$$V2/(V2+V3)=0.65, \text{ hence,}$$

$$V2=0.65 \times \{V0/(r2-1)-V0/(r1-1)\}$$

$$V3=0.35 \times V2/0.65$$

$$V3=0.35 \times \{V0/(r2-1)-V0/(r1-1)\}.$$

Thus, when the biological sample is diluted with the solution containing the internal standard substance that does not penetrate through the blood cell membrane, the solution containing the internal standard substance that penetrates through the blood cell membrane, or the solution containing the internal standard substance that does not penetrate through the blood cell membrane and the internal standard substance that penetrates through the blood cell membrane, V1, V2 and V3 can be calculated from V0, r1 and r2.

Furthermore, combinations of V0, r1, r2, V1, V2 and V3 allows, for example, the following items to be calculated:
 the amount of plasma or serum (V1);
 the dilution ratio of plasma or serum (r1);

TABLE 4

| | Internal Standard Substance in the Solution | Items That Can Be Calculated |
|---|---|---|
| 1 | The internal standard substance that does not penetrate through the blood cell membrane | The dilution ratio (r1) of the biological sample component that does not penetrate through the blood cell membrane |
| 2 | The internal standard substance that penetrates through the blood cell membrane | The dilution ratio (R2) of the entire blood |
| 3 | The internal standard substance that does not penetrate through the blood cell membrane and the internal standard substance that penetrates through the blood cell membrane | The dilution ratio (r1) of the biological sample component that does not penetrate through the blood cell membrane and the dilution ratio (r2) of the entire blood |

Moreover, when the biological sample is diluted with a solution containing the internal standard substance that does not penetrate through the blood cell membrane, if the volume (V0) of the solution containing the internal standard substance is a prescribed amount, the volume (V1) of the biological sample that does not penetrate through the blood cell membrane can be calculated from the dilution ratio (r1) of the biological sample component that does not penetrate through the blood cell membrane calculated based on the internal standard substance that does not penetrate through the blood cell membrane.

Specifically, V1=V0/(r1−1) can be calculated.

Furthermore, when the biological sample is diluted with a solution containing the internal standard substance 5 that penetrates through the blood cell membrane, if the volume (V0) of the solution containing the internal standard subthe amount of plasma or serum and the blood cell liquid (V1+V2);
 the dilution ratio of the entire blood (r2);
 the amount of blood (V1+V2+V3);
 the dilution ratio of blood {(V0+V1+V2+V3)/(V1+V2+V3)};
 the amount of blood cells (V2+V3);
 the dilution ratio of blood cells {(V0+V2+V3)/(V2+V3)};
 the amount of the blood cell liquid (V 2 );
 the dilution ratio of the blood cell liquid {(V0+V2)/V2};
 the amount of the blood cell solid (V3):
 the dilution ratio of the blood cell solid {(V0+V3)/V3};
 the hematocrit value (%) {(V2+V3)/(V1+V2+V3)×100 (%)} or 1−(blood dilution ratio−1)/(plasma dilution ratio−1);
 the amount of the buffer (V0);

the dilution ratio of the buffer relative to plasma or serum $\{(V0+V1)/V0\}$;

the dilution ratio of the buffer relative to plasma or serum and the blood cell liquid $\{(V0+V1+V2)/V0\}$;

the dilution ratio of the buffer relative to blood $((V0+V1+V2+V3)/V0)$;

the dilution ratio of the buffer relative to the blood cell liquid $\{(V0+V2)/V0\}$;

the dilution ratio of the buffer relative to the blood cell solid $\{(V0+V3)/V0\}$; and the dilution ratio of the buffer relative to blood cells $\{(V0+V2+V3)/V0\}$.

The items that can be calculated using V0, r1, r2, V1, V2 and V3 alone or in combination are not limited to the examples given above.

2. Method of Analysis using an External Standard Substance (External Standard Method)

The present invention provides a method of quantifying a component to be analyzed that is to be quantified in a biological sample after the biological sample such as blood is diluted with a buffer, wherein a dilution ratio of the biological sample is determined using an external standard substance, which is a component in the biological sample, and the component to be analyzed in the biological sample is quantified based on the dilution factor.

With the method of the present invention, it is unnecessary to determine the analyte amount of the biological sample to determine the dilution factor of the biological sample.

A method using the external standard substance will be referred to as the "external standard method". For example, a method using sodium as the external standard substance will be referred to as the "sodium (Na) external standard method".

The dilution factor is determined using the external standard substance, which is a hemostatic component contained in the biological component.

Examples of the biological sample to be analyzed in the present invention include biological samples such as blood, serum, plasma, urine, saliva, lymph, spinal fluid, intercellular fluid, and sweat, with blood, serum, and plasma being particularly preferred. In particular, in a preferred embodiment of the present invention, a trace amount of blood is collected from a subject and diluted with a buffer, blood cells are subsequently separated by filtering or centrifugation, and the component to be analyzed is measured using the obtained plasma or serum. Moreover, in the present invention, a trace amount of the biological sample will suffice because the biological sample is diluted with the diluent buffer. In particular, when the biological sample is blood, the component to be analyzed can be measured using a trace amount, i.e., 200 μL or less, of a blood sample.

The biological sample may be derived from sources such as animals, fishes, and birds, without being limited to humans. Examples of animals include a horse, a cow, a pig, a sheep, a goat a dog, a cat, a mouse, a bear, and a panda.

The biological sample component to be analyzed is not limited, and various substances contained in the biological sample may be analyzed. Examples of such substances include items of biochemical tests in blood used for clinical diagnosis, and markers for various diseases such as tumor markers or hepatitis markers, for example, proteins, sugar, lipids, and low-molecular-weight compounds. Moreover, not only the concentration of a substance but also the activity of a substance with activity such as an enzyme may be measured. Measurement of each of the components to be analyzed can be performed using a known method.

The external standard substance is preferably a substance contained in the biological sample and having high homeostasis, i.e., a substance of which concentration in the biological sample does not show significant physiological variations, and is also preferably a substance of which concentration in the biological sample does not significantly vary between human individuals. Examples of such substances include sodium ($Na^+$), chloride ($Cl^-$), and proteins. Examples of proteins include albumin and total protein in serum, which are contained in blood and have high homeostasis. In particular, sodium is preferred because it has high homeostasis and does not significantly vary between individuals.

The normal value of sodium concentration in human plasma, i.e., the sodium concentration in plasma of healthy individuals, is approximately 135 to 145 mmol/L (mEq/L), and the median is approximately 142 mmol/L. In 95% of subjects, the sodium concentration in plasma falls within the normal range of concentrations. In 2.5% of subjects, the sodium concentration in plasma is lower than the normal range of concentrations, and in 2.5% of subjects, the sodium concentration in plasma is higher than the normal range of concentrations. The dilution factor of the biological sample used as the analyte can be determined based on the concentration of the external standard substance after dilution with the buffer and the average value of the sodium concentration in plasma of healthy individuals. When a biological sample other than blood, serum, or plasma is used as the biological sample, the dilution factor can be determined based on the median of the sodium concentration in the biological sample.

Because a substance contained in the biological sample is used as the external standard substance, it is necessary to use, as the buffer for diluting the biological sample, a buffer that is either free of the external standard substance, or contains the external standard substance only at an extremely low concentration that does not affect the measurement of the external standard substance in the mixture after diluting the biological sample. It is also necessary to use a buffer that is either free of a substance that interferes with the measurement of the external standard substance, or contains such a substance only at an extremely low concentration that does not affect the measurement of the external standard substance in the diluted solution after diluting the biological sample. Such a buffer that is either free of these substances, or contains these substances only at an extremely low concentration that does not affect the measurement of the external standard substance in the mixture after diluting the biological sample, will be referred to as the buffer substantially free of the substances. The sodium concentration in the diluent buffer used in the method of the present invention is 100 nmol/L or less, for example.

For example, when sodium or chloride is used as the external standard substance, the diluent buffer for the biological sample needs to be either free of sodium or chloride, or contains sodium or chloride only in an extremely small amount. The diluent buffer for the biological sample also needs to be either free of sodium, or contains sodium only in an extremely small amount, because sodium affects the quantification of an element belonging to alkali metals or alkaline earth metals. Furthermore, for measuring the target substance to be analyzed in the biological sample, in order to prevent degradation or denaturation of the target substance to be analyzed, the diluent buffer for the biological sample needs to be a buffer having a pH near that of the biological sample, i.e., pH 6.5 to 8.0, preferably pH 7.0 to 7.5, and more preferably pH 7.4. Furthermore, in the present invention, for measuring the biological component in the blood diluted with the buffer, the buffer components should not cause denaturation or affect the stability of the biological component to be measured. Because no buffer has previously existed which has a buffering capacity around pH 7.4 and is free of sodium or chloride, it has been impossible to use sodium or chloride as the external standard substance. The present invention has developed a new buffer having a buffering capacity around pH 7.4 and free of sodium or chloride to enable the use of sodium or chloride as the external standard substance.

An example of the buffer may be a buffer obtained by mixing a combination of an amino alcohol compound such as 2-amino-2-methyl-1-propanol (AMP), 2-ethylaminoethanol, N-methyl-D-glucamine, diethanolamine, or triethanolamine, as an alkaline substance free of sodium, chloride, or an element belonging to alkali metals or alkaline earth metals, with a Good's buffer, which is a buffer having a pKa near pt 7.4, such as HEPES (2-[4-(2-hydoxyethyl)-1-piperazinyl]ethanesulfonic acid) (pKa=7.55), TES (N-tris(hydroxymethyl)methyl-2-aminoethanesulfonic acid) (pKa=7.50), MOPS (3-morpholinopropanesulfonic acid) (pKa=7.20), or BES (N,N-bis(2-hydroxyethyl)-2-aminoethanesulfonic acid) (pKa=7.15), as an acidic compound. In particular, the combination of 2-amino-2-methyl-1-propanol (AMP) with HEPES, TES, MOPS, or BES is preferred, and the combination of 2-amino-2-methyl-1-propanol (AMP) with HEPES is more preferred.

To prepare the above-described buffer, the amino alcohol and the Good's buffer may be mixed at a concentration ratio of 1:2 to 2:1, preferably 1:1.5 to 1.5:1, and more preferably 1:1. While the concentration of the buffer is not limited, the concentration of the amino alcohol or the Good's buffer is 0.1 to 1000 mM/L, preferably 1 to 500 mM/L, and more preferably 10 to 100 mM/L.

For the purpose of stably keeping the component to be analyzed, the buffer may contain a chelating agent, a surfactant, an antimicrobial agent, a preservative, a coenzyme, a saccharide, an inhibitor, and the like. Examples of chelating agents include ethylenediaminetetraacetate (EDTA), citrate, and oxalate. Examples of surfactants include cationic surfactants, anionic surfactants, ampholytic surfactants, and nonionic surfactants. Examples of preservatives include sodium azide and antibiotics. Examples of coenzymes include pyridoxal phosphate, magnesium, and zinc. Examples of saccharides include mannitol, dextrose, and oligosaccharides. Examples of inhibitors include sodium dodecyl sulfate, mercury, and heparin. In particular, the addition of mannitol and pyridoxal phosphate can stabilize the blood cell membrane and enzymes, and the addition of three to four types of antibiotics or antimicrobial agents can suppress the growth of bacteria partially included from the surface of a finger during the collection of blood from the finger, thereby stabilizing the degradation of the biological component due to bacteria.

When whole blood is used as the biological sample, because of the need to filter the blood cell component in the diluted blood, hemolysis of blood cells can be prevented by using, as the osmolality of the buffer, an osmolality equal to or higher than the osmolality of blood (285 mOsm/kg). The osmolality can be adjusted to be isotonic by using a salt, a saccharide, a buffer, or the like that does not affect the quantification of the biological component to be measured.

The present invention also encompasses the above-described buffer used by the method of the present invention for using the dilution factor of the biological sample.

Chloride ($Cl^-$) or protein, which is an external standard substance, can also be measured using a known method. For example, chloride can be measured using a method of measuring the absorbance. Because amylase is activated by chloride ions, the absorbance can be measured based on the reaction rate. Protein can be measured using the Biuret method, Bradford method, or Lowry method, for example. Albumin can be measured using the bromcresol green method, which is a pigment method.

Examples of methods of measuring sodium in the biological sample used as the external standard diluted with the buffer include the use of a flame photometer, the atomic absorption method, and the ion selective electrode method. When blood is used as the biological sample in the present invention, the amount of the sample prepared by collecting a trace amount of blood from a finger and diluting the blood with the buffer is as small as approximately 150 µL. For the measurement of biochemical components or 10 or more items of immunological tests, it is necessary to measure sodium used as the external standard substance, using a trace amount, i.e., several microliters, of the sample. Moreover, because of the need to analyze a large amount of sample, the method of the present invention needs to be adaptable to a commercial biochemical or immunological automated analyzer.

In sodium measurement, the enzyme activity of the galactosidase enzyme is activated by sodium ions. Thus, the present invention has developed an enzymatic measurement method for measuring sodium using several microliters of a sample with a very low concentration of sodium (24 mmol/L or less) diluted with the buffer. In this enzymatic measurement method, a trace amount of sodium in the diluted biological sample is measured by utilizing the phenomenon in which β-galactosidase is activated by sodium, and utilizing the proportional relationship between the sodium concentration in the sample diluted with the buffer and the galactosidase activity. This method is efficient and highly economical in that it is adaptable to a biochemical or immunological automated analyzer, and does not require a separate equipment for measuring sodium.

In the above-described method of measuring sodium, a biological sample such as blood is diluted with the diluent buffer and is further diluted with purified water; a first reagent of a buffer comprising β-galactosidase is added in an amount 10 to 30 times the amount by volume of the diluted sample; the mixture is heated at 30 to 45° C. for 2 to 20 minutes; a second reagent of a substrate solution comprising o-nitrophenyl-β-D-galactopyranoside is added in half the amount of the first reagent; and absorbance is measured at a primary wavelength of 410 nm and a secondary wavelength of 658 nm. More specifically, the biological sample such as blood is diluted with the diluent buffer and is further diluted approximately 5-fold with purified water. To 1 to 10 µL, preferably 3 µL, of the diluted mixture of the biological sample and the buffer, 30 to 100 µL, preferably 52 µL, of the buffer comprising β-galactosidase as the first reagent is added such that the volume ratio of the buffer comprising β-galactosidase relative to the diluted mixture of the biological sample and the buffer becomes 10 to 30, preferably 15 to 25. The mixture is then heated at 30 to 45° C., preferably at 37° C., for 2 to 20 minutes, preferably 5 minutes, and then 25 µL of the substrate solution comprising o-nitrophenyl-β-D-galactopyranoside as the second reagent is added. The absorbance is subsequently measured at a primary wavelength of 410 nm and a secondary wavelength of 658 nm, thereby measuring the sodium concentration.

The method of determining the dilution factor of the biological sample of the present invention is desirably performed as follows.

To 50 to 500 μL of the buffer, 10 to 200 μL of the biological sample is added and mixed. In this case, the volume of the buffer is preferably not less than 3 to 4 times the volume of the biological sample. For example, when the biological sample is blood, a trace amount, i.e., 65 μL, of the blood sample is added and mixed into 280 μL of the buffer. When the biological sample is blood, blood cells such as erythrocytes and leucocytes are removed after dilution. The blood cells may be removed through a filter, or may be removed by subjecting the diluted blood sample to centrifugation. The component to be analyzed is measured using the diluted plasma sample from which the blood cells have been removed. When a trace amount, i.e., 65 μL, of the blood sample is added into 280 μL of the buffer, approximately 30 μL of plasma is contained in 65 μL of the blood sample, and thus, the plasma is diluted approximately 10-fold. When blood is used as the biological sample, the blood and the diluent buffer may be mixed such that, when calculated as plasma, the plasma is diluted 5- to 20-fold, preferably 5- to 16-fold, more preferably 5- to 10-fold, and particularly preferably approximately 8- to 10-fold.

The concentration of the external standard substance in the diluted plasma sample is also measured simultaneously. The concentration of the component to be analyzed in the blood can be calculated by determining a dilution factor of the blood based on the concentration of the external standard substance, and multiplying the measured value of the component to be analyzed in the diluted plasma sample by the dilution factor.

When blood is used as the biological sample, the blood is diluted with the diluent buffer, and blood cells are subsequently removed therefrom. Thus, the remaining sample is plasma, which will be referred to as the diluted plasma. In this case, therefore, the dilution factor of plasma is determined.

The dilution factor of plasma can be determined in accordance with the following calculation method using the formula (I), with the use of the external standard substance.

The method described below uses a plasma sample obtained by diluting blood with the diluent buffer, and filtering the diluted blood through a filter.

Calculation Method 1

$$X = \frac{A}{B} \quad (1)$$

wherein

A: absorbance of a normal median of the concentration of the external standard substance in plasma;

B: absorbance of the external standard substance in the diluted plasma; and

X: a plasma dilution factor.

When sodium is used as the external standard substance, the absorbance of sodium may be determined. The absorbance of 142 mmol/L of sodium may be used as the absorbance of the normal median of the sodium concentration in plasma.

3. Method of Measurement using an Internal Standard Substance and an External Standard Substance (Hybrid Method)

The present invention provides a method of quantifying a component to be analyzed that is to be quantified in a biological sample after the biological sample such as blood is diluted with a buffer, wherein a dilution ratio of the biological sample is determined using an internal standard substance and an external standard substance, and the component to be analyzed in the biological sample is quantified based on the dilution factor.

With the method of the present invention, it is unnecessary to determine the analyte amount of the biological sample to determine the dilution factor of the biological sample.

In determining the dilution factor by using the internal standard substance and the external standard substance in combination, the external standard substance is used to correct the dilution factor obtained with the internal standard substance to accurately determine the dilution factor. The method of determining the dilution factor of the biological sample of the present invention, which uses both the internal standard substance and the external standard substance, may be referred to as the "hybrid method".

When the dilution factor of the biological sample is determined using only the internal standard substance, the biological sample is diluted with the diluent buffer containing the internal standard substance. Thus, if the amount of the biological sample is small, the dilution factor will become excessively high, which reduces the reliability of the dilution factor determined based on the concentration of the internal standard substance. The hybrid method of the present invention can compensate for this drawback of the method using the internal standard substance, by using the external standard substance. Furthermore, as described below, the biological sample may contain a substance used as the internal standard substance, or the concentration of the external standard substance originally present in the biological sample may fall outside the range of normal values. Even in these cases, the hybrid method allows an accurate dilution factor to be determined by compensating for the drawback of each of the methods.

As the biological sample to be analyzed in the present invention, the biological samples described in "2. Method of Analysis Using an External Standard Substance (External Standard Method)" above can be used, and the sources of the biological sample are also as described in the section 2. (External Standard Method) above.

The biological sample component to be analyzed is also as described in the section 2. (External Standard Method) above.

The internal standard substance is added into the buffer used for diluting the biological sample to give a predetermined concentration. The following substances are used as the internal standard substance: a substance that is either not at all contained, or contained only in an extremely small amount, in the biological sample; a substance that does not interfere with the measurement of the component to be analyzed in the biological sample; a substance that is not degraded by the action of enzymes in vivo in the biological sample; a substance stable in the buffer; a substance that does not penetrate through the blood cell membrane and is not contained in blood cells; a substance that is not adsorbed to a storage container for the buffer; and a substance that permits the use of a detection system that allows accurate measurement. Examples of such substances include those described in "1. Method of Analysis Using an Internal Standard Substance (Internal Standard Method)" above. Particularly preferred is an element belonging to alkali metals or alkaline earth metals that is stable even after being stored in the buffer for a long period of time, and that is not natively present in the biological sample.

Examples of such elements belonging to alkali metals include Li (lithium), Rb (rubidium), Cs (cesium), and Fr (francium), and examples of such elements belonging to alkaline earth metals include Sr (strontium), Ba (barium), and Ra (radium), with Li being particularly preferred.

Glycerol-3-phosphate described in JP Patent Publication (Kokai) No. 2003-161729 A can also be used.

The concentration at which the internal standard substance is added into the buffer used for diluting the biological sample is not limited as long as the concentration of the internal standard substance after dilution can be measured. The internal standard substance may be added at a concentration of 0.1 to 1000 mM/L, for example, preferably 0.1 to 100 mM/L, and more preferably 0.5 to 10 mM/L. For example, when lithium is used as the internal standard substance, lithium may be added at the above-described concentration into the buffer used for diluting the biological sample.

The dilution factor of the biological sample used as the analyte can be determined based on the concentration of the internal standard substance in the diluted solution of the biological sample after dilution with the buffer and the concentration of the internal standard substance added into the buffer used for dilution.

The range of dilution factors of the sample when the sample is added into the buffer containing the internal standard substance is from 5- to 20-fold, and preferably 5- to 15-fold, although not limited thereto.

The external standard substance is preferably a substance contained in the biological sample and having high homeostasis, i.e., a substance of which concentration in the biological sample does not show significant physiological variations, and is also preferably a substance of which concentration in the biological sample does not significantly vary between human individuals. Examples of such substances include sodium ($Na^+$), chloride ($Cl^-$), and proteins. Examples of proteins include albumin and total protein in serum, which are contained in blood and have high homeostasis. In particular, sodium is preferred because it has high homeostasis and does not significantly vary between individuals.

The normal value of sodium concentration in human plasma. i.e., the sodium concentration in plasma of healthy individuals, is approximately 135 to 145 mmol/L (mEq/L), and the normal median is approximately 142 mmol/L. In 95% of subjects, the sodium concentration in plasma falls within the normal range of concentrations. In 2.5% of subjects, the sodium concentration in plasma is lower than the normal range of concentrations, and in 2.5% of subjects, the sodium concentration in plasma is higher than the normal range of concentrations. The dilution factor of the biological sample used as the analyte can be determined based on the concentration of the external standard substance after dilution with the buffer and the average value of the sodium concentration in plasma of healthy individuals. When a biological sample other than blood, serum, or plasma is used as the biological sample, the dilution factor can be determined based on the median of the sodium concentration in the biological sample.

A more accurate dilution factor can be determined by determining the dilution factor of the biological sample used as the analyte based on the concentration of the internal standard substance in the biological sample after dilution with the buffer added and the concentration of the internal standard substance added into the buffer used for dilution, and by correcting the dilution factor calculated based on the concentrations of the internal standard substance, by using the concentration of the external standard substance in the biological sample after dilution and the concentration of the external standard substance contained in the biological sample.

Because a substance contained in the biological sample is used as the external standard substance, it is necessary to use, as the buffer for diluting the biological sample, a buffer that is either free of the external standard substance, or contains the external standard substance only at an extremely low concentration that does not affect the measurement of the external standard substance in the mixture after diluting the biological sample. It is also necessary to use a buffer that is either free of a substance that interferes with the measurement of the external standard substance and the internal standard substance, or contains such a substance only at an extremely low concentration that does not affect the measurement of the internal standard substance or the external standard substance in the diluted solution after diluting the biological sample. Such a buffer that is either free of these substances, or contains these substances only at an extremely low concentration that does not affect the measurement of the internal standard substance or the external standard substance in the mixture after diluting the biological sample, will be referred to as the buffer substantially free of the substances. The sodium concentration in the diluent buffer used in the method of the present invention is 100 nmol/L or less, for example.

For example, when sodium or chloride is used as the external standard substance, the diluent buffer for the biological sample needs to be either free of sodium or chloride, or contains sodium or chloride only in an extremely small amount. As the internal standard substance, an element belonging to alkali metals or alkaline earth metals is used, and thus, the diluent buffer for the biological sample needs to be either free of the element belonging to alkali metals or alkaline earth metals used as the internal standard substance or a substance analogous to these elements, or contains such a substance only in an extremely small amount. The diluent buffer for the biological sample also needs to be either free of sodium, or contains sodium only in an extremely small amount, because sodium affects the quantification of the element belonging to alkali metals or alkaline earth metals. Furthermore, for measuring the target substance to be analyzed in the biological sample, in order to prevent degradation or denaturation of the target substance to be analyzed, the diluent buffer for the biological sample needs to be a buffer having a pH near that of the biological sample, i.e., pH 6.5 to 8.0, preferably pH 7.0 to 7.5, and more preferably pH 7.4. Furthermore, in the present invention, for measuring the biological component in the blood diluted with the buffer, the buffer components should not cause denaturation or affect the stability of the biological component to be measured. Because no buffer has previously existed which has a buffering capacity around pH 7.4 and is free of sodium or chloride, it has been impossible to use sodium or chloride as the external standard substance. The present invention has developed a new buffer having a buffering capacity around pH 7.4 and free of sodium or chloride to enable the use of sodium or chloride as the external standard substance.

An example of the buffer may be a buffer obtained by mixing a combination of an amino alcohol compound such as 2-amino-2-methyl-1-propanol (AMP), 2-ethylaminoethanol, N-methyl-D-glucamine, diethanolamine, or triethanolamine, as an alkaline compound free of sodium, chloride, or an element belonging to alkali metals or alkaline earth metals, with an acidic Good's buffer, which is a buffer having a pKa near pH 7.4, such as HEPES (2-[4-(2-hydoxyethyl)-1-piperazinyl]ethanesulfonic acid) (pKa=7.55), TES (N-tris(hydroxymethyl)methyl-2-aminoethanesulfonic acid) (pKa=7.50). MOPS (3-morpholinopropanesulfonic acid) (pKa=7.20), or BES (N,N-bis(2-hydroxyethyl)-2-aminoethanesulfonic acid) (pKa=7.15). In particular, the combination of 2-amino-2-methyl-1-propanol (AMP) with HEPES, TES, MOPS, or BES is preferred, and the combination of 2-amino-2-methyl-1-propanol (AMP) with HEPES is more preferred.

To prepare the above-described buffer, the amino alcohol and the Good's buffer may be mixed at a concentration ratio of 1:2 to 2:1, preferably 1:1.5 to 1.5:1, and more preferably 1:1. While the concentration of the buffer is not limited, the concentration of the amino alcohol or the Good's buffer is 0.1 to 1000 mM/L, preferably 1 to 500 mM/L, and more preferably 10 to 100 mM/L.

For the purpose of stably keeping the component to be analyzed, the buffer may contain a chelating agent, a surfactant, an antimicrobial agent, a preservative, a coenzyme, a saccharide, an inhibitor, and the like. Examples of chelating agents include ethylenediaminetetraacetate (EDTA), citrate, and oxalate. Examples of surfactants include cationic surfactants, anionic surfactants, ampholytic surfactants, and nonionic surfactants. Examples of preservatives include sodium azide and antibiotics. Examples of coenzymes include pyridoxal phosphate, magnesium, and zinc. Examples of saccharides include mannitol, dextrose, and oligosaccharides. Examples of inhibitors include sodium dodecyl sulfate, mercury, and heparin. In particular, the addition of mannitol and pyridoxal phosphate can stabilize the blood cell membrane and enzymes, and the addition of three to four types of antibiotics or antimicrobial agents can suppress the growth of bacteria partially included from the surface of a finger during the collection of blood from the finger, thereby stabilizing the degradation of the biological component due to bacteria.

When whole blood is used as the biological sample, because of the need to filter the blood cell component in the diluted blood, hemolysis of blood cells can be prevented by using, as the osmolality of the buffer, an osmolality equal to or higher than the osmolality of blood (285 mOsm/kg). The osmolality can be adjusted to be isotonic by using a salt, a saccharide, a buffer, or the like that does not affect the quantification of the biological component to be measured.

The present invention also encompasses the above-described buffer used by the hybrid method of the present invention for using the dilution factor of the biological sample. The buffer can be used not only for the hybrid method of the present invention, but also for the quantitative analysis method using an external standard (external standard method) and the quantitative analysis method using an internal standard (internal standard method).

The element belonging to alkali metals or alkaline earth metals used as the internal standard substance can be measured using a known method. For example, a substance that forms a chelate complex with the element belonging to alkali metals or alkaline earth metals may be added, and the absorbance of the chelate complex formed may be measured. Examples of substances that form chelate complexes with the element belonging to alkali metals or alkaline earth metals include porphyrin derivatives such as polyvalent halogenated porphyrin compounds (such as polyfluoroporphyrin), for example. Alternatively, the absorbance of the element itself may be measured using atomic absorption spectroscopy. Specifically, lithium added as the internal standard substance into the buffer can be measured with a biochemical automated analyzer, by utilizing a chelate colorimetric method (halogenated porphyrin chelate method: perfluoro-5,10,15,20-tetraphenyl-21H,23H-porphyrin). This method allows easy measurement for a number of analytes using a trace amount of sample.

Chloride ($Cl^-$) or protein, which is an external standard substance, can also be measured using a known method described in the section 2. (External Standard Method) above.

In the method of the present invention, an accurate dilution factor can be determined by determining the dilution factor using the hybrid method, which uses the two standard substances, i.e., an element belonging to alkali metals or alkaline earth metals, such as lithium, as the internal standard substance, and a substance contained in the biological sample, such as sodium ($Na^+$), chloride ($Cl^-$), or protein, as the external standard substance, and by correcting the dilution factor determined using the internal standard substance, by using the external standard substance.

Lithium carbonate is used as a pharmaceutical for improving the manic state of mania and manic-depressive illness. Lithium carbonate is administered into a subject in need of treatment at a dose of several hundreds of milligrams to one thousand and several hundreds of milligrams per day. Lithium is therefore contained in the biological sample of the subject receiving the administration of lithium carbonate, and thus, an accurate dilution factor cannot be determined if lithium only is used as the internal standard.

On the other hand, as described above, the normal range of sodium concentrations in blood of healthy individuals is approximately 135 to 145 mmol/L (mEq/L). In approximately 5% of subjects, even if they are healthy individuals, the sodium concentration in blood falls outside the range of normal values. In approximately 2.5% of subjects, even if they are healthy individuals, the sodium concentration in blood is lower than the above-described range of normal values. In approximately 2.5% of subjects, even if they are healthy individuals, the sodium concentration in blood is higher than the above-described range of normal values. In these subjects, when sodium only is used as the external standard, the dilution factor cannot be accurately determined.

As described above, even when the subject is receiving the administration of an element belonging to alkali metals or alkaline earth metals, such as lithium, as the pharmaceutical, or when the concentration of sodium ($Na^+$), chloride ($Cl^-$), or protein in blood falls outside the range of normal values, the dilution factor determined using the internal standard substance is corrected by using the external standard substance, which allows the drawbacks of both methods to be compensated for, leading to an accurate determination of the dilution factor of the biological sample.

The method of determining the dilution factor of the biological sample of the present invention is desirably performed as follows.

10 to 200 µL of the biological sample is added and mixed into 50 to 500 µL of a buffer to which the internal standard substance has been added in advance at a predetermined concentration. In this case, the volume of the buffer is preferably not less than 3 to 4 times the volume of the biological sample. For example, when the biological sample is blood, a trace amount, i.e., 65 µL, of the blood sample is added and mixed into 280 µL of the buffer containing the internal standard. When the biological sample is blood, blood cells such as erythrocytes and leucocytes are removed after dilution. The blood cells may be removed through a filter, or may be removed by subjecting the diluted blood sample to centrifugation. The component to be analyzed is measured using the diluted plasma sample from which the blood cells have been removed. When a trace amount, i.e., 65 μL, of the blood sample is added into 280 μL of the buffer containing the internal standard, approximately 30 μL of plasma is contained in 65 μL of the blood sample, and thus, the plasma is diluted approximately 10-fold. When blood is used as the biological sample, the blood and the diluent buffer may be mixed such that, when calculated as plasma, the plasma is diluted 5- to 20-fold, preferably 5- to 16-fold, more preferably 5- to 10-fold, and particularly preferably approximately 8- to 10-fold.

The concentration of the internal standard substance and the concentration of the external standard substance in the diluted plasma sample are also measured simultaneously. The concentration of the component to be analyzed in the blood can be calculated by determining a dilution factor of the blood based on the concentration of the internal standard substance and the concentration of the external standard substance, and multiplying the measured value of the component to be analyzed in the diluted plasma sample by the dilution factor.

When blood is used as the biological sample, the blood is diluted with the diluent buffer, and blood cells are subsequently removed therefrom. Thus, the remaining sample is plasma, which will be referred to as the diluted plasma. In this case, therefore, the dilution factor of plasma is determined.

The dilution factor of plasma can be determined using the following three calculation methods, which uses the internal standard substance and the external standard substance.

The methods described below use a plasma sample obtained by diluting blood with the diluent buffer containing the internal standard substance, and filtering the diluted blood through a filter. Lithium is used as the internal standard substance, and sodium is used as the external standard substance.

Calculation Method 1

A: absorbance of the internal standard substance in the buffer containing the internal standard substance;

B: absorbance of the internal standard substance in the diluted plasma;

C: absorbance of a normal median of the concentration of the external standard substance in plasma;

D: absorbance of the external standard substance in the diluted plasma; and

X: a plasma dilution factor.

The diluted plasma herein refers to plasma obtained by diluting the blood sample with the diluent buffer, and removing blood cells therefrom. When lithium is used as the internal standard substance, and sodium is used as the external standard substance, the lithium concentration can be represented by the absorbance obtained by measuring the lithium concentration using the chelate colorimetric method, for example. The sodium concentration can be represented by the absorbance measured using the enzymatic measurement method, for example. The normal median of the sodium concentration in plasma corresponds to the median of healthy individuals, and the absorbance of 142 mmol/L of sodium may be used as the absorbance of the normal median of the sodium concentration in plasma. This value is a known value. This is also the case in calculation methods 2 and 3 described below.

The dilution factor X of the plasma diluted with the buffer can be determined based on the following calculation method (1) or (2):

$$X = \frac{A+C}{B+D} \quad (1)$$

$$X = \frac{\sqrt{(A^2+C^2)}}{\sqrt{(B^2+D^2)}} \quad (2)$$

The concentration of the biological component, which is the component to be analyzed, in the diluted plasma, or enzyme activity is quantified, and the value of quantification is multiplied by the dilution factor determined using the formula (1) or (2). In this way, the component to be analyzed in the original plasma can be quantified.

Calculation Method 2

B: absorbance of the internal standard substance in the diluted plasma;

D: absorbance of the external standard substance in the diluted plasma; and

X: a plasma dilution factor.

The dilution factor of plasma can be determined using the following formula (3):

$$X = a \times (B+D) \pm b \quad (3)$$

(a and b are coefficients).

In the calculation method 2, data of B+D and the dilution factor are acquired in advance to prepare a regression line represented by $X = a \times (B+D) \pm b$.

The concentration of the biological component, which is the component to be analyzed, in the diluted plasma, or enzyme activity is quantified, and the value of quantification is multiplied by the dilution factor determined using the formula (3). In this way, the component to be analyzed in the original plasma can be quantified.

Calculation Method 3

A: absorbance of the internal standard substance in the buffer containing the internal standard substance;

B: absorbance of the internal standard substance in the diluted plasma;

C: absorbance of a normal median of the concentration of the external standard substance in plasma;

D: absorbance of the external standard substance in the diluted plasma;

B': a correction value for correcting the absorbance of the internal standard substance in the diluted plasma, obtained by using the dilution factor calculated from the absorbance of the external standard substance; and X: a plasma dilution factor.

When it is assumed that the dilution factor X of the internal standard substance (lithium, for example) and the external standard substance (sodium, for example) is the same, the following formula can be derived:

$$X = A/B = C/D.$$

The correction value B' for correcting the absorbance variation of the internal standard substance (lithium, for example) by using the dilution factor of the external standard substance (sodium, for example) is determined using the following formula:

$$(B') = (A \times D)/C.$$

A is divided by the correction value B' for correcting the absorbance variation of the internal standard substance (lithium, for example) to determine the dilution factor of the internal standard substance (lithium, for example) corrected by using the external standard substance (sodium, for example):

$$X = A/B' \quad (4).$$

The concentration of the biological component, which is the component to be analyzed, in the diluted plasma, or enzyme activity is quantified, and the value of quantification is multiplied by the dilution factor determined using the formula (4). In this way, the component to be analyzed in the original plasma can be quantified.

EXAMPLES

Examples of the present invention will be described hereinafter.

1. Method of Analysis using an Internal Standard (Internal Standard Method)

Example 1-1

Fifty samples of venous blood were each examined by adding 60 μL of a whole blood sample containing EDTA-2Na into 200 μL of a blood dilution buffer obtained by adding maltose as an internal standard substance into a diluent buffer. Correlations between measured values of plasma obtained by centrifugation of undiluted whole blood and measured values of diluted plasma, determined by multiplying measured values of diluted plasma by a dilution factor determined with the internal standard, were examined. As a result, as shown in FIG. 1, satisfactory correlations were obtained in the tests for enzyme activities (transaminase; ALT, γ-glutamyl transferase; GGT) and the lipid tests (triglyceride; TG, LDL-cholesterol, glucose, hemoglobin A1c).

Example 1-2

Fifty samples of venous blood were each examined by adding 60 μL of a whole blood sample containing EDTA-2Na into 200 μL of a blood dilution buffer, obtained by adding, into a blood diluent buffer, ethanolamine as an internal standard to be distributed into blood cells and plasma.

Figure 5:
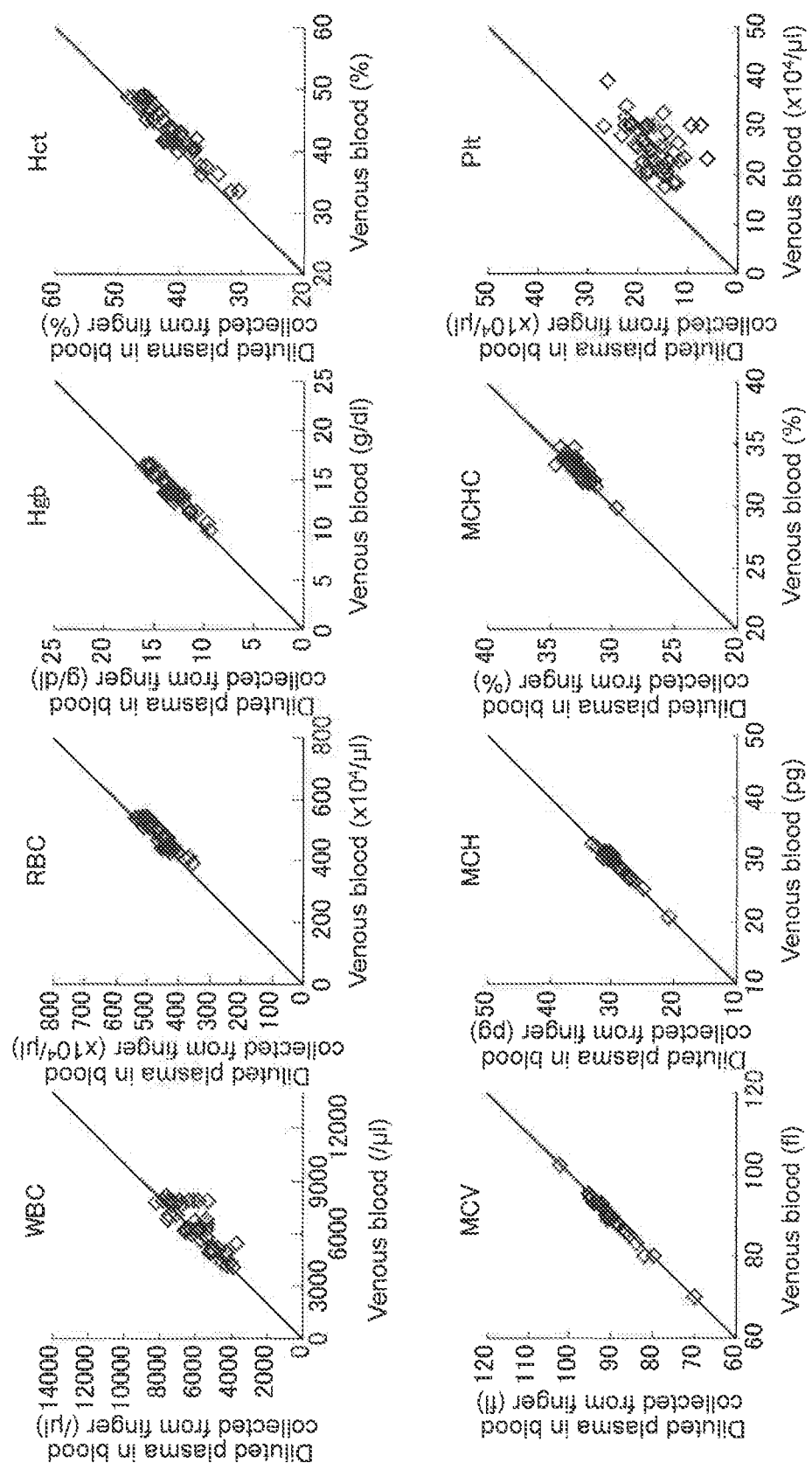
FIG. 5 shows correlation diagrams obtained by counting leucocytes (WBC), erythrocytes (RBC), the hemoglobin concentration (Hgb), the hematocrit value (Hct), and the platelet count (Plt), using, as samples, EDTA-2Na-containing whole blood in the blood collected from the vein and diluted whole blood obtained by diluting this whole blood with a blood dilution buffer.

FIG. 5 shows correlation diagrams obtained by counting leucocytes (WBC), erythrocytes (RBC), the hemoglobin concentration (Hgb), the hematocrit value (Hct), and the platelet count (Plt), using, as samples, EDTA-2Na-containing whole blood in the blood collected from the vein and diluted whole blood obtained by diluting this whole blood with the blood dilution buffer. From these diagrams, satisfactory correlations are observed except for the platelet count.

Example 1-3

Figure 6:
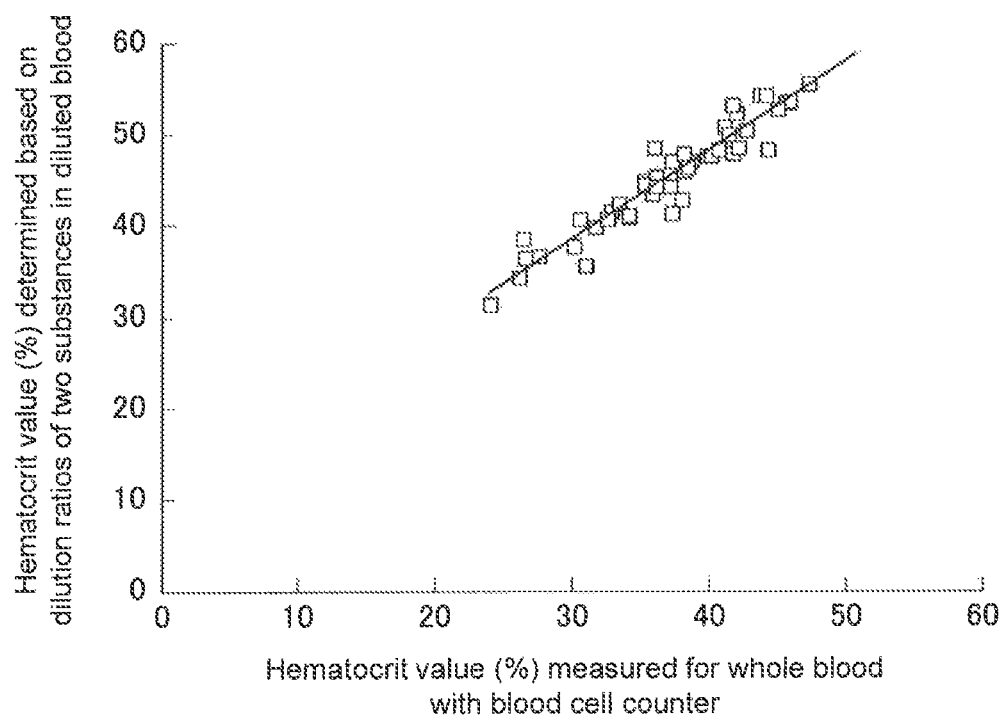
FIG. 6 shows a correlation diagram between the hematocrit value representing the volume of blood cells in the blood, determined based on a formula, by using the plasma dilution ratio determined with maltose as the internal standard and the whole blood dilution ratio determined with ethanolamine, and the hematocrit value determined for whole blood using a blood cell counter.

A correlation between the hematocrit value representing the volume of blood cells in the blood, determined based on a formula, by using the plasma dilution ratio determined with maltose as the internal standard and the whole blood dilution ratio determined with ethanolamine, and the hematocrit value determined for whole blood using a blood cell counter, was examined. The results are shown in FIG. 6. The correlation was satisfactory and practical.

2. Method of Analysis using an External Standard Substance (External Standard Method)

Example 2-1 Quantitative Analysis using a Trace Amount of a Blood Sample (1) Measurement of the External Standard Substance (Sodium) and Calculation of the Dilution Factor 65 μL of a trace amount of a blood sample was added and mixed into 280 μL of a buffer, blood cells were filtered out, and the concentration of each of the external standard substance and a biological component was measured for diluted plasma as a sample, using a biochemical automated analyzer.

As the diluent buffer for diluting the blood sample, a buffer at pH 7.4 obtained by mixing a combination of 2-amino-2-methyl-1-propanol and HEPES (2-[4-(2-hydoxyethyl)-1-piperazinyl]ethanesulfonic acid) was used.

Table 5 shows the composition of the buffer.

TABLE 5

Composition of the Diluent Buffer Containing Sodium as the External Standard

| Substance Name | Concentration |
| --- | --- |
| HEPES | 50 mM/L |
| 2-Amino-2-methyl-1-propanol (AMP) | 50 mM/L |
| D-Mannitol | 284 mM/L |
| EDTA-2K | 0.8 mM/L |
| PALP: Pyridoxal Phosphate | 0.05 mM/L |
| Thiabendazol | 0.0001% (w/v) |
| Piperacillin Sodium | 0.0003% (w/v) |
| Amikacin Sulfate | 0.0003% (w/v) |
| Kanamycin Sulfate | 0.0005% (w/v) |
| Meropenem Trihydrate | 0.0005% (w/v) |
| Osmolality | 355 mOsm/Kg |
| pH 7.4 | |

Sodium contained in the blood sample was used as the external standard substance.

For measurement of a trace amount of sodium in the diluted plasma, an enzymatic measurement method was developed which utilizes the phenomenon in which β-galactosidase is activated by sodium, and utilizes the proportional relationship between the sodium concentration in the sample diluted with the buffer and the galactosidase activity.

Table 6 shows the compositions of reagents for measuring sodium.

TABLE 6

Compositions of Reagents for Measuring Sodium

| | Reagent | Concentration |
| --- | --- | --- |
| First Reagent | pH 8.0, HEPES•LiOH | 100 mmol/L |
| | D-Mannitol | 60 mmol/L |
| | N•Acetylcysteine | 30 mmol/L |
| | Magnesium Sulfate | 1.52 mmol/L |
| | β-Galactosidase | 1.1 kU/L |
| | Triton X-100 | 0.05% |
| Second Reagent | pH 8.0, HEPES•LiOH | 100 mmol/L |
| | o-Nitrophenyl-β-D-Galactpyranoside | 15 mmol/L |

Measurement was performed as follows, using the reagents for measuring sodium shown in Table 6.

65 μL of whole blood was added into 280 μL of the diluent buffer to dilute plasma (approximately 30 μL) in the whole blood approximately 10-fold. This diluted plasma was diluted 4.5-fold with purified water, and 52 μL of a β-galactosidase buffer (first reagent) was added to 3 μL of the diluted plasma. The mixture was heated at 37° C. for 5 minutes. To this mixture, 26 μL of a substrate solution of o-nitrophenyl-β-D-galactopyranoside (second reagent) was added. Then, a change in the rate of absorbance for 1 minute was determined by measuring the absorbance at a primary wavelength of 410 nm and a secondary wavelength of 658 nm, using the model JCA-BM 6050 biochemical automated analyzer from JEOL Ltd. FIG. 1 shows a calibration curve plotting the sodium concentration vs the variation in absorbance. The calibration curve showed linearity passing through the origin point at up to 24 mmol/L, which indicated that sodium could be quantified.

(2) Measurement of the External Standard Substance (Chloride)

The following reagents were used.

1) First Reagent:

A solution obtained by adding 2 U/ml pancreatic amylase and 10 mmol/L EDTA into 0.1 mol/L MES.NaOH buffer at pH 6.0.

2) Second Reagent:

5 mmol/L 2-chloro-4-nitrophenyl maltose solution.

The method of measuring chloride was as follows.

150 µL of the first reagent was added into 5 µL of the sample, the mixture was heated at 37° C. for 5 minutes, and subsequently, 50 µL of the second reagent was added. One minute thereafter, a variation in absorbance at 405 nm for 2 minutes was determined.

Figure 8:
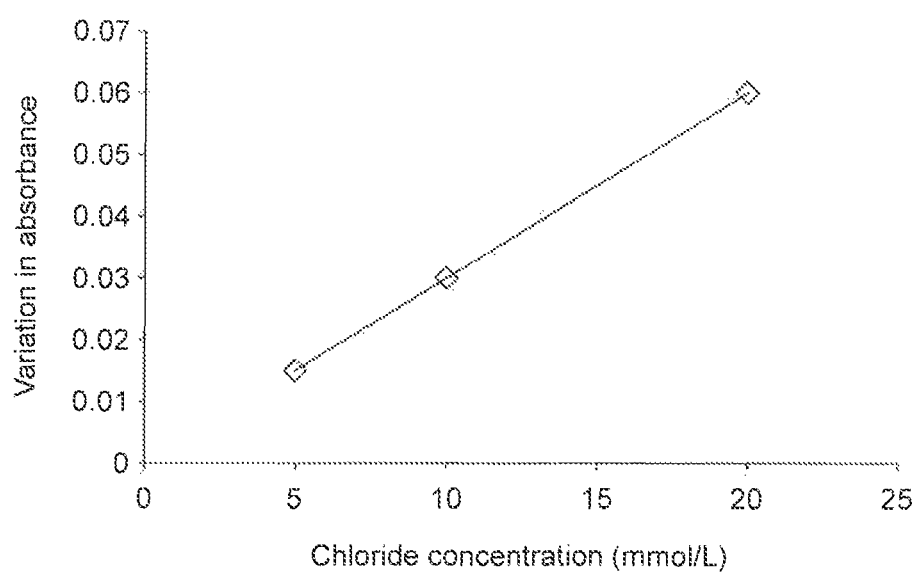
FIG. 8 is a diagram showing the linearity of the chloride measurement method.

FIG. 8 shows a calibration curve plotting the chloride concentration vs the variation in absorbance.

(3) Correlations between a Trace Amount of a Blood Sample and Venous Plasma

Table 7 shows statistical values of correlations between measured values of plasma and measured values of diluted plasma determined based on the dilution factor of the external standard substance (sodium). The measurement was performed using the model JCA-BM 6050 biochemical automated analyzer from JEOL Ltd. Table 7 shows the correlations between plasma data (measured values of plasma) and biochemical test data of diluted plasma (measured values of diluted plasma) determined using the dilution factor (X: 8-fold dilution) determined based on the following formula (I) using the absorbance (A) measured for 142 mmol/L of sodium and the absorbance (B) of sodium in the diluted plasma. Plasma measurement for each of the test items was performed using a conventional method. Measurement of the diluted plasma was performed under optimized conditions, by increasing the volume of the sample more than a volume conventionally used. As shown in Table 7, the correlations for the 13 items of biochemical tests are satisfactory, and biochemical test data in the original plasma can be derived from the trace amount of blood.

$$X = \frac{A}{B} \quad (1)$$

TABLE 7

Correlations between Plasma and Diluted Plasma Obtained with the Sodium External Standard Method

| | Na External Standard Method Regression Equation for the Correlations between the Diluted Plasma and Plasma | | |
|---|---|---|---|
| | Slope | Intercept | Correlation Coefficient |
| Total Protein | 0.82 | 1.40 | 0.751 |
| Albumin | 0.85 | 0.64 | 0.822 |
| AST | 0.98 | 0.45 | 0.990 |
| ALT | 1.00 | −0.06 | 0.998 |
| γGT | 1.02 | −0.59 | 0.998 |
| Total Cholesterol | 0.97 | 5.58 | 0.973 |
| HDL-Cholesterol | 0.97 | 1.52 | 0.987 |
| LDL-Cholesterol | 0.98 | 3.30 | 0.990 |
| Triglyceride | 1.05 | −3.83 | 0.999 |

TABLE 7-continued

Correlations between Plasma and Diluted Plasma Obtained with the Sodium External Standard Method

| | Na External Standard Method Regression Equation for the Correlations between the Diluted Plasma and Plasma | | |
|---|---|---|---|
| | Slope | Intercept | Correlation Coefficient |
| Urea Nitrogen | 0.99 | 0.10 | 0.993 |
| Creatinine | 0.98 | 0.02 | 0.966 |
| Uric Acid | 1.01 | −0.03 | 0.994 |
| Glucose | 0.97 | 2.00 | 0.994 |

3. Method of Analysis using an Internal Standard Substance and an External Standard Substance (Hybrid Method)

Example 3-1 Quantitative Analysis using a Trace Amount of a Blood Sample (1) Measurement of the Internal Standard Substance (Lithium or Glycerol-3-Phosphate) and the External Standard Substance (Sodium) and Calculation of the Dilution Factor 65 µL of a trace amount of a blood sample was added and mixed into 280 µL of a buffer containing the internal standard substance, blood cells were filtered out, and the concentration of each of the internal standard substance, the external standard substance, and a biological component was measured for diluted plasma as a sample, using a biochemical automated analyzer.

As the diluent buffer for diluting the blood sample, a buffer at pH 7.4 obtained by mixing a combination of 2-amino-2-methyl-1-propanol and HEPES (2-[4-(2-hydoxyethyl)-1-piperazinyl]ethanesulfonic acid) was used.

Table 8 shows the composition of the buffer containing the internal standard substance.

TABLE 8

Composition of the Diluent Buffer Containing Lithium as the Internal Standard Substance

| Substance Name | Concentration |
|---|---|
| Substance Name | 50 mM/L |
| 2-Amino-2-methyl-1-propanol (AMP) | 50 mM/L |
| D-Mannitol | 284 mM/L |
| Lithium Chloride | 1 mM/L |
| EDTA-2K | 0.8 mM/L |
| PALP: Pyridoxal Phosphate | 0.05 mM/L |
| Thiabendazol | 0.0001% (w/v) |
| Piperacillin Sodium | 0.0003% (w/v) |
| Amikacin Sulfate | 0.0003% (w/v) |
| Kanamycin Sulfate | 0.0005% (w/v) |
| Meropenem Trihydrate | 0.0005% (w/v) |
| Osmolality | 355 mOsm/Kg |
| pH 7.4 | |

Lithium was used as the internal standard substance, and 1 mM/L of lithium chloride was added into the diluent buffer. Sodium contained in the blood sample was used as the external standard substance.

Lithium contained in the buffer as the internal standard substance was measured using a chelate colorimetric method (halogenated porphyrin chelate method: perfluoro-5,10,15,20-tetraphenyl-21H,23H-porphyrin).

For measurement of a trace amount of sodium in the diluted plasma, an enzymatic measurement method was developed which utilizes the phenomenon in which β-galactosidase is activated by sodium, and utilizes the proportional relationship between the sodium concentration in the sample diluted with the buffer and the galactosidase activity.

Table 9 shows the compositions of reagents for measuring sodium.

TABLE 9

Compositions of Reagents for Measuring Sodium

| | Reagent | Concentration |
|---|---|---|
| First Reagent | pH 8.0, HEPES•LiOH | 100 mmol/L |
| | D-Mannitol | 60 mmol/L |
| | N-Acetylcysteine | 30 mmol/L |
| | Magnesium Sulfate | 1.52 mmol/L |
| | β-Galactosidase | 1.1 kU/L |
| | Triton X-100 | 0.05% |
| Second Reagent | pH 8.0, HEPES•LiOH | 100 mmol/L |
| | o-Nitrophenyl-β-D-Galactpyranoside | 15 mmol/L |

Measurement was performed as follows, using the reagents for measuring sodium shown in Table 9.

Figure 7:
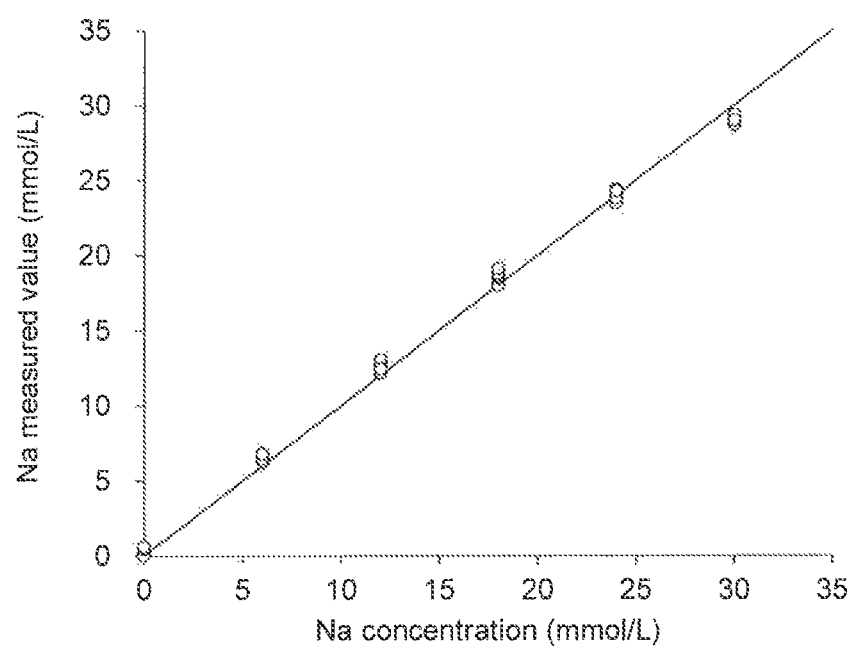
FIG. 7 is a diagram showing the linearity of the enzymatic measurement method for sodium.

65 μL of whole blood was added into 280 μL of the diluent buffer to dilute plasma (approximately 30 μL) in the whole blood approximately 10-fold. This diluted plasma was diluted 4.5-fold with purified water, and 52 μL of a β-galactosidase buffer (first reagent) was added to 3 μL of the diluted plasma. The mixture was heated at 37° C. for 5 minutes. To this mixture, 26 μL of a substrate solution of o-nitrophenyl-β-D-galactopyranoside (second reagent) was added. Then, a change in the rate of absorbance for 1 minute was determined by measuring the absorbance at a primary wavelength of 410 nm and a secondary wavelength of 658 nm, using the model JCA-BM 6050 biochemical automated analyzer from JEOL Ltd. FIG. 7 shows a calibration curve plotting the sodium concentration vs the variation in absorbance. The calibration curve showed linearity passing through the origin point at up to 24 mmol/L, which indicated that sodium could be quantified.

TABLE 10

Method of Measuring Lithium

| | Reagent | Concentration |
|---|---|---|
| First Reagent (Chelate Reagent) | perfluoro-5,10,15,20-tetraphenyl-21H,23H-porphyrin | 0.05% (W/V) |
| | Dimethylsulfoxide | 5% (W/V) |
| | Triethanolamine | 2% (W/V) |
| | Polyethylene-Glycol-t-Octylphenyl Ether | 2% (W/V) |
| | Sodium Dodecyl Sulfate | 2% (W/V) |

Lithium was measured in accordance with the following method, using the measurement reagent shown in Table 10.

65 μL of whole blood was added into 280 μL of the diluent buffer to dilute plasma (approximately 30 μL) in the whole blood approximately 10-fold. This diluted plasma was diluted 4.5-fold with purified water, and 55 μL of the chelate reagent (first reagent) was added to 5 μL of the diluted plasma. The mixture was heated at 37° C. for 10 minutes, and the absorbance was measured at a primary wavelength of 545 nm and a secondary wavelength of 596 nm, using the model JCA-BM 6050 biochemical automated analyzer from JEOL Ltd.

Figure 9:
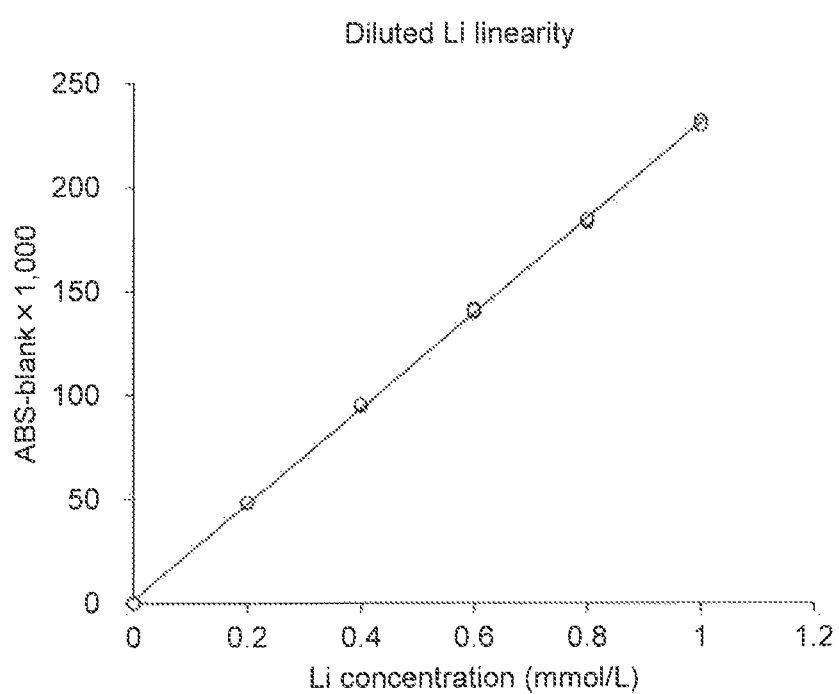
FIG. 9 is a diagram showing the linearity between lithium concentration and absorbance.

FIG. 9 shows a calibration curve plotting the lithium concentration vs the absorbance. The calibration curve showed linearity passing through the origin point at up to 1 mmol/L, which indicated that lithium could be quantified.

When glycerol-3-phosphate was used as the internal standard substance, measurement was performed in accordance with the following method. 65 μL of whole blood was added into 280 μL of the diluent buffer to dilute plasma (approximately 30 μL) in the whole blood approximately 10-fold. This diluted plasma was diluted 4.5-fold with purified water, and 50 μL of the first reagent (peroxidase) was added to 9 μL of the diluted plasma. The mixture was heated at 37° C. for 5 minutes. Five minutes after the addition of 25 μL of the second reagent (glycerol-3-phosphate oxidase), the absorbance was measured at a primary wavelength of 596 nm and a secondary wavelength of 884 nm, using the model JCA-BM 6050 biochemical automated analyzer from JEOL Ltd. The calibration curve showed linearity passing through the origin point at up to 4 mmol/L, which indicated that glycerol-3-phosphate could be quantified.

The reagent compositions shown in Table 11 were used in the method of measuring glycerol-3-phosphate.

TABLE 11

Method of Measuring Glycerol-3-Phosphate

| First Reagent | pH 7.0, 50 mmol/L HEPES•NaOH Buffer |
| | 7.7 mmol/L Sodium Azide |
| | 20 mmol/L Potassium Chloride |
| | 0.6 mmol/L ADPS |
| | 5 KU/L Peroxidase |
| Second Reagent | pH 7.0, 50 mmol/L HEPES•NaOH Buffer |
| | 8 mmol/L Sodium Azide |
| | 20 mmol/L Potassium Chloride |
| | 2 mmol/L 4-Aminoantipyrine |
| | 16 KU/L Glycerol-3-Phosphate Oxidase |

(2) Correlations between Trace Amounts of Blood Samples and Venous Plasma

Figures 1, 10:
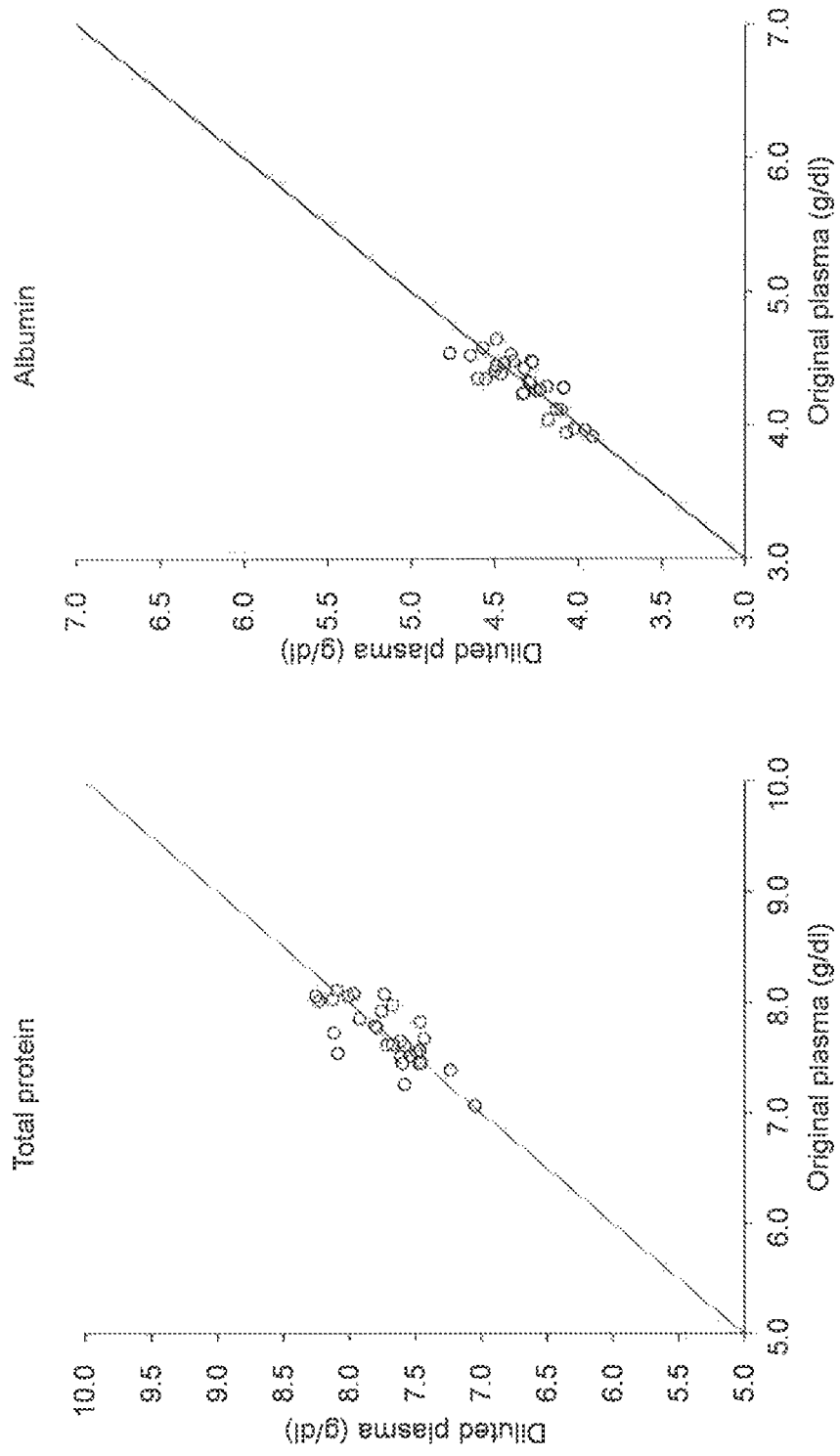
Figures 3, 10:
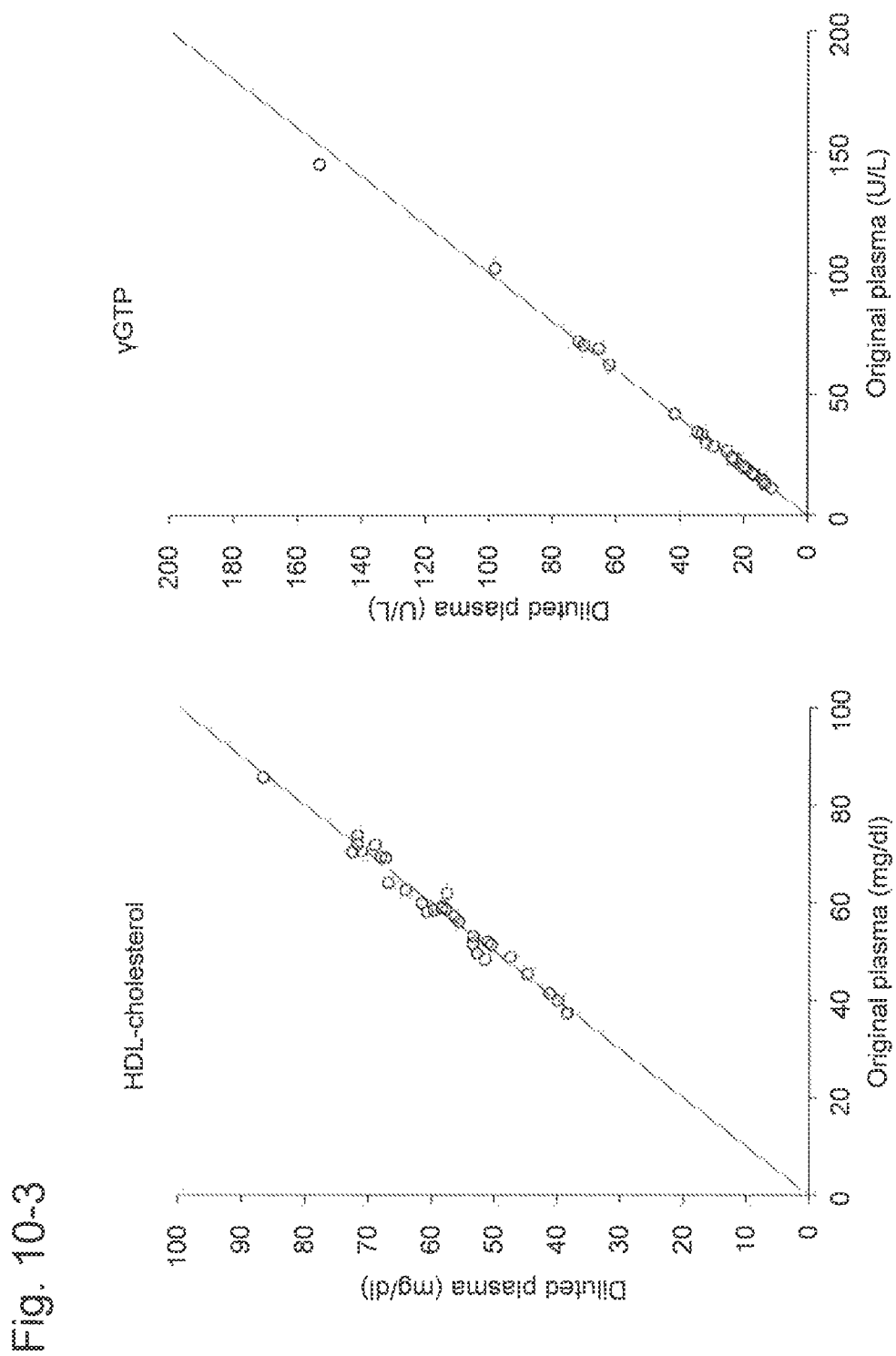
Figures 4, 10:
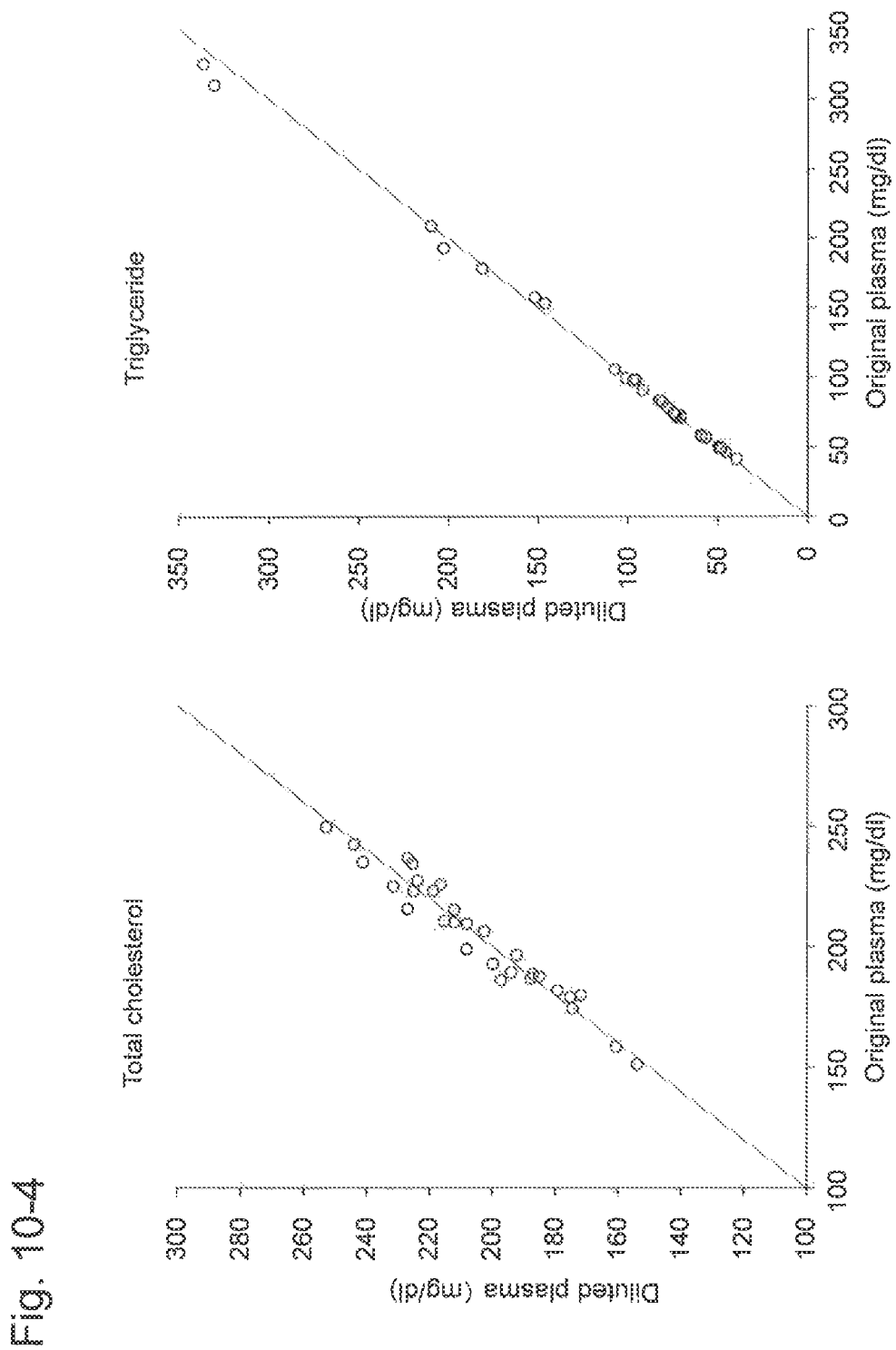
Figures 5, 10:
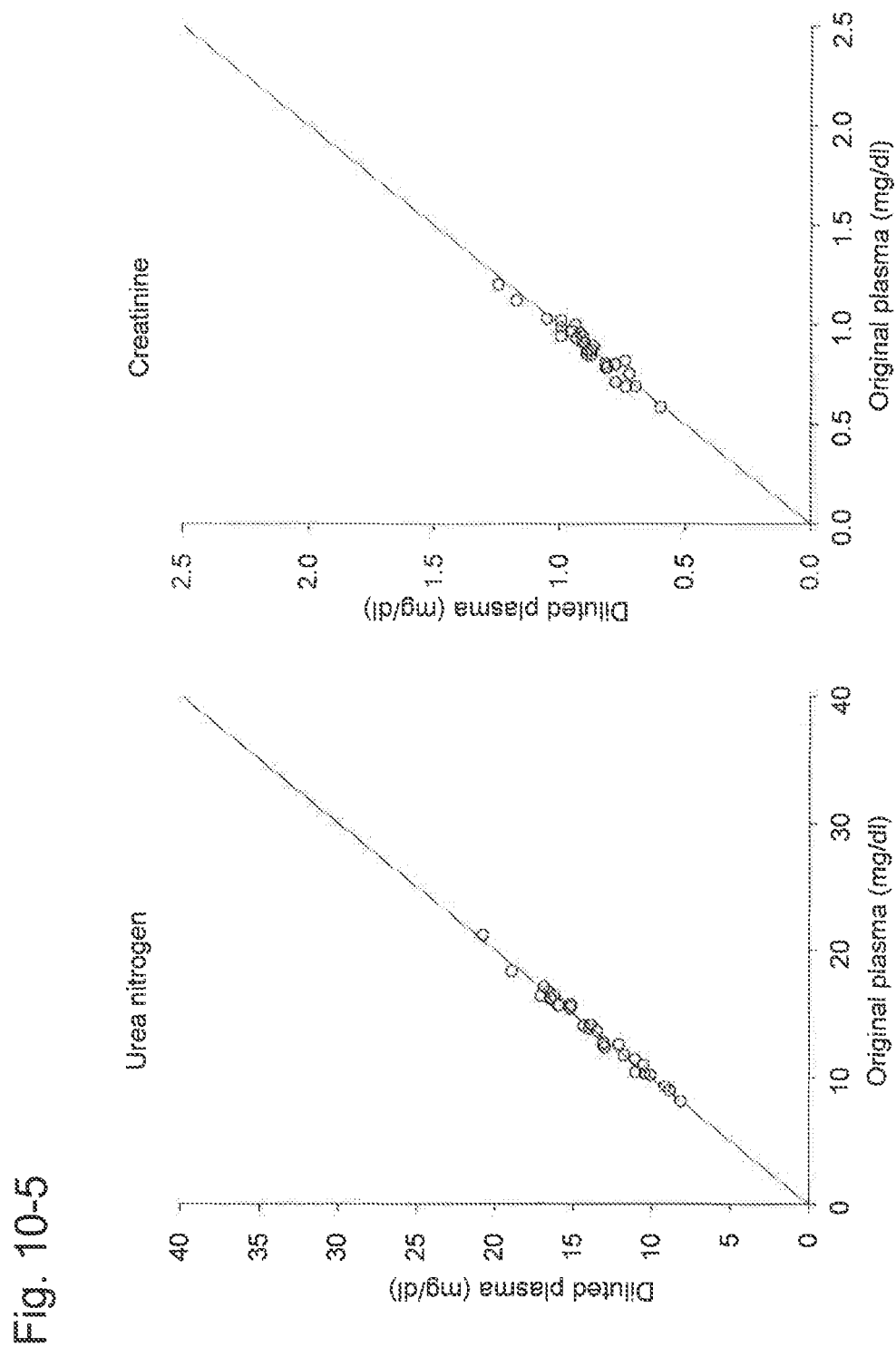
Figures 6, 10:
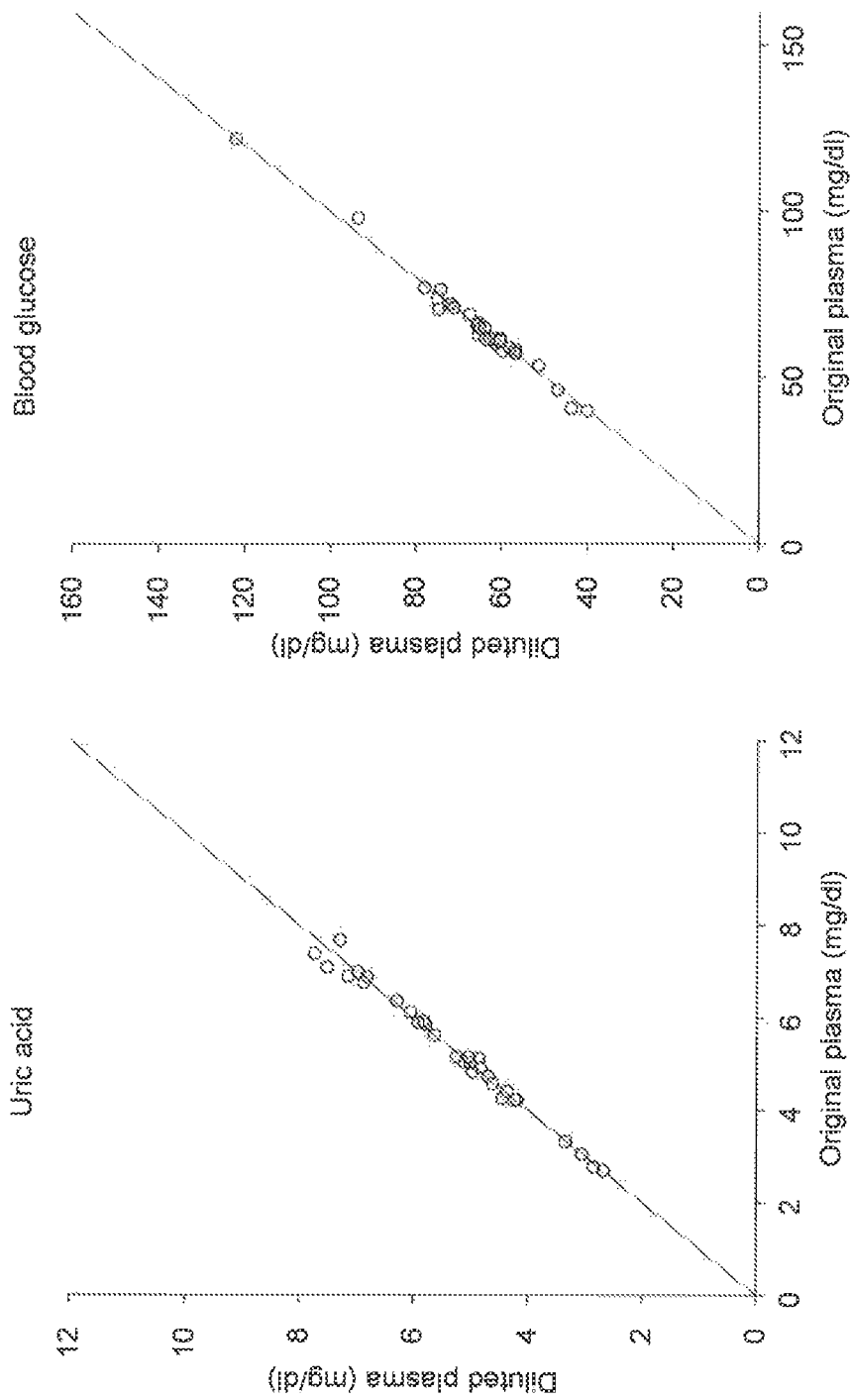

FIGS. 10-1 to 10-6 show correlation diagrams between measured values of plasma and diluted plasma measured for items of biochemical tests using the model JCA-BM 6050 biochemical automated analyzer from JEOL Ltd. The x-axis represents plasma data (measured values of plasma), and the y-axis represents biochemical test data of diluted plasma (measured values of diluted plasma) determined using the dilution ratio (X: 8-fold dilution) determined with the hybrid method based on the following formula (1), using the absorbance (A) measured for the internal standard substance (lithium) in the diluent buffer, the absorbance (B) measured for the internal standard substance after the addition of plasma, the absorbance (C) measured for 142 mmol/L of sodium, and the absorbance (D) of sodium in the diluted plasma. Plasma measurement for each of the test items was performed using a conventional method. Measurement of the diluted plasma was performed under optimized conditions, by increasing the volume of the sample more than a volume conventionally used. As shown in FIGS. 10-1 to 10-6, the correlations for the 13 items of biochemical tests are satisfactory, and biochemical test data in the original plasma can be derived from the trace amount of blood.

$$X = \frac{A + C}{B + D} \quad (1)$$

Table 12 shows statistical values of correlations between measured values of plasma and measured values of diluted plasma determined with the hybrid method, which uses the internal standard substance (lithium) and the external standard substance (sodium) in combination.

TABLE 12

Correlations Obtained with the Hybrid Method Using the Internal Standard Substance (Lithium) and the External Standard Substance (Sodium) Correlations between Measured Values of Plasma and Measured Values of Diluted Plasma Obtained with the Hybrid Method Using the Internal Standard Substance and the External Standard Substance

| Item | Correlation Coefficient | Regression Equation |
| --- | --- | --- |
| Total Protein | 0.751 | y = 0.98 + 1.4 |
| Albumin | 0.822 | y = 0.97 + 0.6 |
| AST | 0.990 | y = 0.98 + 0.5 |
| ALT | 0.998 | y = 1.00 − 0.1 |
| γGTP | 0.998 | y = 1.02 − 0.6 |
| Total Cholesterol | 0.973 | y = 0.97 + 5.6 |
| HDL-Cholesterol | 0.987 | y = 0.97 + 1.5 |
| LDL-Cholesterol | 0.990 | y = 0.98 + 3.3 |
| Triglyceride | 0.999 | y = 1.05 − 3.8 |
| Urea Nitrogen | 0.993 | y = 0.99 + 0.1 |
| Creatinine | 0.966 | y = 0.98 + 0.0 |
| Uric Acid | 0.994 | y = 1.01 + 0.0 |
| Glucose | 0.994 | y = 0.97 + 2.0 |

Example 3-2 Correlations between Measured Values of Plasma and Diluted Plasma for Items of Biochemical Tests Table 13 shows correlations between measured values of plasma and diluted plasma measured for items of biochemical tests using the model JCA-BM 6050 biochemical automated analyzer from JEOL Ltd. The x-axis represents plasma data (measured values of plasma), and the y-axis represents biochemical test data of diluted plasma (measured values of diluted plasma) determined using the dilution ratio (X: 8-fold dilution) determined with the hybrid method based on the formula (1) shown in Example 3-1, using the absorbance (A) measured for the internal standard substance (glycerol-3-phosphate) in the diluent buffer, the absorbance (B) measured for the internal standard substance after the addition of plasma, the absorbance (C) measured for 142 mmol/L of sodium, and the absorbance (D) of sodium in the diluted plasma. Plasma measurement for each of the test items was performed using a conventional method. Measurement of the diluted plasma was performed under optimized conditions, by increasing the volume of the sample more than a volume conventionally used. As shown in Table 13, the correlations for the 13 items of biochemical tests are satisfactory, and biochemical test data in the original plasma can be derived from the trace amount of blood.

Table 13 shows statistical values of correlations between measured values of plasma and measured values of diluted plasma determined with the hybrid method, which uses the internal standard substance (glycerol-3-phosphate) and the external standard substance (sodium) in combination.

TABLE 13

Correlations between the Plasma Measurement Method and the Hybrid Method Using Glycerol-3-Phosphate and Sodium Correlations between Measured Values of Plasma and Measured Values of Diluted Plasma Obtained with the Hybrid Method Using the Internal Standard Substance and the External Standard Substance

| Item | Correlation Coefficient | Regression Equation |
| --- | --- | --- |
| Total Protein | 0.834 | y = 1.08 − 0.6 |
| Albumin | 0.789 | y = 1.04 − 0.2 |
| AST | 0.977 | y = 0.98 + 3.5 |
| ALT | 0.983 | y = 1.00 + 2.9 |
| γGTP | 0.996 | y = 1.01 + 1.4 |
| Total Cholesterol | 0.975 | y = 1.02 − 8.0 |
| HDL-Cholesterol | 0.973 | y = 0.96 + 3.9 |
| LDL-Cholesterol | 0.989 | y = 1.02 − 3.5 |
| Triglyceride | 0.998 | y = 1.04 + 2.0 |
| Urea Nitrogen | 0.982 | y = 0.96 + 0.4 |
| Creatinine | 0.970 | y = 0.99 − 0.1 |
| Uric Acid | 0.975 | y = 0.99 + 0.1 |
| Glucose | 0.979 | y = 0.97 + 2.0 |

Example 3-3 Effects of the Combined use of the Internal Standard Substance (Li) and the External Standard Substance (Na) upon the Measurement Error and Accuracy of Test Data (1) Effects of the use of Sodium in Plasma as the External Standard Substance upon the Dilution Factor The sodium concentration in plasma of healthy individuals shows very small physiological variations in the individuals and between individuals, and the referential range (normal range) of sodium concentrations in plasma is from 135 to 145 mmol/L. When the sodium concentration in diluted plasma obtained by diluting a blood sample with a diluent buffer and removing blood cells therefrom is measured using an enzymatic method with high sensitivity by utilizing the median, i.e., 142 mmol/L, of the sodium concentration of healthy individuals, the sodium concentration can be accurately measured up to 0 to 30 mmol/L. Furthermore, for samples each having an upper limit of 135 mmol/L or a lower limit of 145 mmol/L of the referential range, measurement can be made within an error of ±2%, by correcting the dilution factor based on 142 mmol/L as the reference.

As shown in Table 14, however, in 2.5% of healthy individuals of all the healthy individuals, the sodium concentration in plasma falls outside the upper or lower limit of the referential range and thus, an error of ±4% or more is produced for plasma having a sodium concentration of 136 mmol/L or 148 mmol/L. With the hybrid method which uses the combination of the method of determining the dilution factor using lithium as the internal standard substance and the method of determining the dilution factor using sodium as the external standard substance, an error of ±4% or more can be reduced by half, as shown in Table 14. In Table 14, the "Na External Standard" section in the column of the dilution factor shows dilution factors determined based on only the concentration of sodium as the external standard substance, and the "Na—Li Correction: Correction with the Hybrid Method" section shows dilution factors determined based on both the concentration of sodium as the external standard substance and the concentration of lithium as the internal standard substance. The dilution factors in the "Correction with the Hybrid Method" were calculated using the formula (1) shown in Example 3-1. Table 14 shows errors produced in measured values of plasma cholesterol determined with the two methods, i.e., the method of determining the dilution factor using sodium only and the method of determining the dilution factor using the hybrid method. The use of the hybrid method was found to reduce the errors by half.

TABLE 14

Effects of the Use of Sodium in Plasma as the External Standard Substance upon the Dilution Factor

| Na Concentration | Na Concentration in Plasma (mmol/L) | Dilution Factor | | Total Cholesterol Concentration (mg/dl) and Measurement Error | | | |
|---|---|---|---|---|---|---|---|
| | | Na External Standard | Correction with the Hybrid Method | Na External Standard | Na Error % | Correction with the Hybrid Method | Error % in the Hybrid Method |
| Lower Limit or Less | 136 | 9.11 | 9.31 | 191.5 | −4.2 | 195.8 | −2.1 |
| Median | 142 | 9.51 | 9.51 | 200.0 | 0.0 | 200.0 | 0.0 |
| Upper Limit or More | 148 | 9.91 | 9.71 | 208.5 | 4.2 | 204.2 | 2.1 |

(2) Effects of the use of Lithium as the Internal Standard Substance upon the Dilution Factor When lithium is added as the internal standard substance into a buffer for diluting blood, the lithium concentration is diluted in accordance with the amount of plasma in the blood. In the method of determining the dilution factor of plasma in this case, the amount of plasma added is large at a dilution factor of up to approximately 8- to 10-fold, and thus, the difference between the concentrations before and after the addition of plasma is large. Thus, the coefficient of variation for the reproducibility of the dilution factor is 2% or less. At a dilution factor of 12- to 16-fold, however, the amount of plasma added is smaller, and thus, the coefficient of variation for the dilution factor increases to 4 to 5%.

As shown in Table 15, the reproducibility was approximately 3% at a dilution factor of 12- to 16-fold, as determined using the correction with the hybrid method, and accurate data were also obtained for subjects from which blood could not be readily collected. At a dilution ratio of 16-fold for a subject having a plasma cholesterol concentration of 210 mg/dl, when the dilution factor is calculated using lithium only as the internal standard substance and the measured value is corrected, a variation of 199 to 221 mg/dl is produced, and thus, the subject is determined as hyperlipidemia (220 mg/dl or more). In Table 15, the "Li Internal Standard" section shows dilution factors determined based on only the concentration of lithium as the internal standard substance, the "Na External Standard" section shows dilution factors determined based on only the concentration of sodium as the external standard substance, and the "Correction with the Hybrid Method" section shows dilution factors determined based on both the concentration of sodium as the external standard substance and the concentration of lithium as the internal standard substance. The dilution factors in the "Correction with the Hybrid Method" were calculated using the formula (1) shown in Example 3-1.

On the other hand, when correction is made using a measured value determined based on the dilution factor calculated using the combination of lithium as the internal standard substance and sodium as the external standard substance, a variation of 204 to 216 mg/dl is produced, and thus, the subject is determined as a healthy individual.

Therefore, a highly accurate measured value can be obtained using the correction with the hybrid method.

TABLE 15

Effects of the Method Using Lithium as the Internal Standard Substance, the Method Using Sodium as the External Standard Substance, and the Hybrid Method upon the Reproducibility (CV %) of the Dilution Factor

| Dilution Factor | Reproducibility | Li Internal Standard | Na External Standard | Correction with the Hybrid Method |
|---|---|---|---|---|
| 6-Fold | Average | 5.91 | 6.01 | 5.96 |
| | CV (%) | 1.49 | 1.83 | 1.57 |
| 8-Fold | Average | 7.85 | 7.97 | 7.91 |
| | CV (%) | 2.71 | 1.21 | 1.98 |
| 10-Fold | Average | 9.61 | 10.00 | 9.81 |
| | CV (%) | 1.59 | 2.14 | 1.78 |
| 12-Fold | Average | 11.53 | 11.86 | 11.69 |
| | CV (%) | 3.34 | 2.34 | 3.24 |
| 14-Fold | Average | 13.43 | 14.09 | 14.09 |
| | CV (%) | 4.07 | 2.71 | 3.26 |
| 16-Fold | Average | 15.75 | 15.35 | 15.35 |
| | CV (%) | 5.13 | 2.12 | 3.49 |

Table 15 shows the effects of the method using lithium as the internal standard substance, the method using sodium as the external standard substance, and the hybrid method upon the reproducibility (CV %) of the dilution factor, at plasma dilution factors of 6- to 16-fold.

The hybrid method provided reproducibility higher than that obtained using the internal standard method alone.

INDUSTRIAL APPLICABILITY

According to the present invention, as described above, easy and accurate quantification can be performed for plasma in a biological sample such as a trace and unknown amount of a whole blood sample collected from inside the body through a finger or the like of a subject, as well as any component in the biological sample. The volume ratio of blood cells (hematocrit value), which indicates the degree of anemia, can also be determined. This allows analysis of the biological sample collected from the subject such as blood to be accurately made, even though a trace amount of the sample such as blood may be collected, which can be done by the subject on his/her own, and even after a long period of time has passed from the collection. The present invention can therefore be effectively used for medical examination of the subject, and is highly industrially applicable.

Furthermore, the method of the present invention in which a trace amount of blood is collected has no restrictions on the time or place for collecting blood, and thus, is applicable to cases where the subject cannot find time to go to a medical institution, events of accidents, telemedicine, health care, and the like. The method of the preset invention can also find an individual with a presymptomatic stage at an early stage, for example, and thus, can contribute to savings in health care costs. Furthermore, the method allows efficient measurement of a large volume of samples with a commercial biochemical automated analyzer. The measured test data can be transmitted to a smart phone, and used on a daily basis for a system for health care or finding a disease at an early stage.

REFERENCE SIGNS LIST

1: blood
2: plasma (serum)
3: blood cells
4: buffer
5: internal standard substance
6: blood diluted solution

We claim:

1. A method of quantitative analysis of a component to be analyzed in a blood sample,-the method comprising:
   (a) diluting a trace amount of the blood sample with a diluent buffer;
   (b) measuring a concentration of an external standard substance in the blood sample diluted with the diluent buffer by absorbance, a Biuret method, a Bradford method, a Lowry method, a bromocresol green method, enzyme methods, using a flame photometer, using atomic absorption, or using an ion selective electrode, wherein the external standard substance is selected from the group consisting of sodium,
   wherein the external standard substance is a component homeostatically present comprised at a predetermined concentration in the blood sample prior to the dilution of the blood sample, and
   wherein the diluent buffer has a pH 6.5 to 8.0 and is substantially free of the external standard substance; and
   (c) calculating the dilution factor of the blood sample from the concentration of the external standard substance measured in (b).

2. The method of quantitative analysis according to claim 1, wherein the diluent buffer comprises
   an amino alcohol compound selected from the group consisting of 2-amino-2-methyl-1-propanol, 2-ethylaminoethanol, N-methyl-D-glucamine, diethanolamine, and triethanolamine, and
   a buffering agent selected from the group consisting of HEPES (2-[4-(2-hydoxyethyl)-1-piperazinyl]ethanesulfonic acid), TES (N-tris(hydroxymethyl)methyl-2-aminoethanesulfonic acid), MOPS (3-morpholinopropanesulfonic acid), and BES (N,N-bis(2-hydroxyethyl)-2-aminoethanesulfonic acid), and
   wherein the diluent buffer has buffering action at pH 7.4.

3. The method of quantitative analysis according to claim 1, wherein the diluent buffer is substantially free of sodium and chloride.

4. The method of quantitative analysis according to claim 1, wherein sodium in the blood sample diluted with the diluent buffer is measured by utilizing a phenomenon in which β-galactosidase undergoes a change in enzyme activity in accordance with sodium ion concentration, and the sodium ion concentration can be quantified from variation in absorbance thereof, the method comprising wherein a biological sample is diluted with the diluent buffer and is further diluted with purified water; a first reagent of a buffer comprising β-galactosidase is added in an amount 10 to 30 times the amount by volume of the sample; the mixture is heated at 30 to 45° C. for 2 to 20 minutes; a second reagent of a substrate solution comprising o-nitrophenyl-β-D-galactopyranoside is added in half the amount of the first reagent; and absorbance is measured at a primary wavelength of 410 nm and a secondary wavelength of 658 nm based on the reaction rate.

5. The method of claim 1, wherein the diluent buffer has a pH near 7.4.

* * * * *